(12) United States Patent
Utsunomiya

(10) Patent No.: US 11,957,316 B2
(45) Date of Patent: Apr. 16, 2024

(54) ENDOSCOPE APPARATUS

(71) Applicant: FUJIFILM Corporation, Tokyo (JP)

(72) Inventor: Daisuke Utsunomiya, Kanagawa (JP)

(73) Assignee: FUJIFILM Corporation, Tokyo (JP)

( * ) Notice: Subject to any disclaimer, the term of this patent is extended or adjusted under 35 U.S.C. 154(b) by 378 days.

(21) Appl. No.: 17/370,618

(22) Filed: Jul. 8, 2021

(65) Prior Publication Data

US 2021/0334941 A1 Oct. 28, 2021

Related U.S. Application Data

(63) Continuation of application No. PCT/JP2020/001032, filed on Jan. 15, 2020.

(30) Foreign Application Priority Data

Jan. 24, 2019 (JP) ................ 2019-009946

(51) Int. Cl.
| | | |
|---|---|---|
| G06K 9/00 | (2022.01) | |
| A61B 1/00 | (2006.01) | |
| A61B 1/06 | (2006.01) | |
| G06T 5/40 | (2006.01) | |
| G06T 5/70 | (2024.01) | |

(52) U.S. Cl.
CPC ...... *A61B 1/0638* (2013.01); *A61B 1/000095* (2022.02); *A61B 1/0005* (2013.01); *A61B 1/0661* (2013.01); *G06T 5/40* (2013.01); *G06T 5/70* (2024.01)

(58) Field of Classification Search
None
See application file for complete search history.

(56) References Cited

U.S. PATENT DOCUMENTS

2015/0042774 A1\* 2/2015 Sugano ............ A61B 1/000094
348/68
2019/0124258 A1 4/2019 Ioka

FOREIGN PATENT DOCUMENTS

| EP | 3 586 719 A1 | 1/2020 |
|---|---|---|
| JP | S63-68127 A | 3/1988 |
| JP | S63-242232 A | 10/1988 |
| JP | H02-85706 A | 3/1990 |
| JP | H04-30831 A | 2/1992 |
| JP | H04-145313 A | 5/1992 |
| JP | 5160276 B2 \* | 3/2013 |
| JP | 2013144039 A \* | 7/2013 |

(Continued)

OTHER PUBLICATIONS

An Office Action mailed by the Japanese Patent Office dated Sep. 13, 2022, which corresponds to Japanese Patent Application No. 2020-568078 and is related to U.S. Appl. No. 17/370,618.

(Continued)

*Primary Examiner* — Wei Wen Yang
(74) *Attorney, Agent, or Firm* — Studebaker & Brackett PC

(57) ABSTRACT

A picked-up image that is obtained from the image pickup of a subject illuminated with illumination light and auxiliary measurement light is acquired. The picked-up image includes at least two first and second spectral images having different wavelength components. A first arithmetic image from which a first noise component hindering the detection of an irradiation position of the auxiliary measurement light is removed by first arithmetic processing based on the first and second spectral images is obtained.

8 Claims, 18 Drawing Sheets

(56) References Cited

FOREIGN PATENT DOCUMENTS

| JP | 5687583 B2 | 3/2015 |
| WO | 2017/212725 A1 | 12/2017 |
| WO | 2017/221335 A1 | 12/2017 |
| WO | 2018/055933 A1 | 3/2018 |

OTHER PUBLICATIONS

The extended European search report issued by the European Patent Office dated Feb. 8, 2022, which corresponds to European Patent Application No. 20744614.7-1126 and is related to U.S. Appl. No. 17/370,618.
An Office Action mailed by the Japanese Patent Office dated Jul. 26, 2022, which corresponds to Japanese Patent Application No. 2020-568078 and is related to U.S. Appl. No. 17/370,618.
International Search Report issued in PCT/JP2020/001032; dated Mar. 3, 2020.
International Preliminary Report on Patentability and Written Opinion issued in PCT/JP2020/001032; dated Jul. 27, 2021.

* cited by examiner

FIG. 11
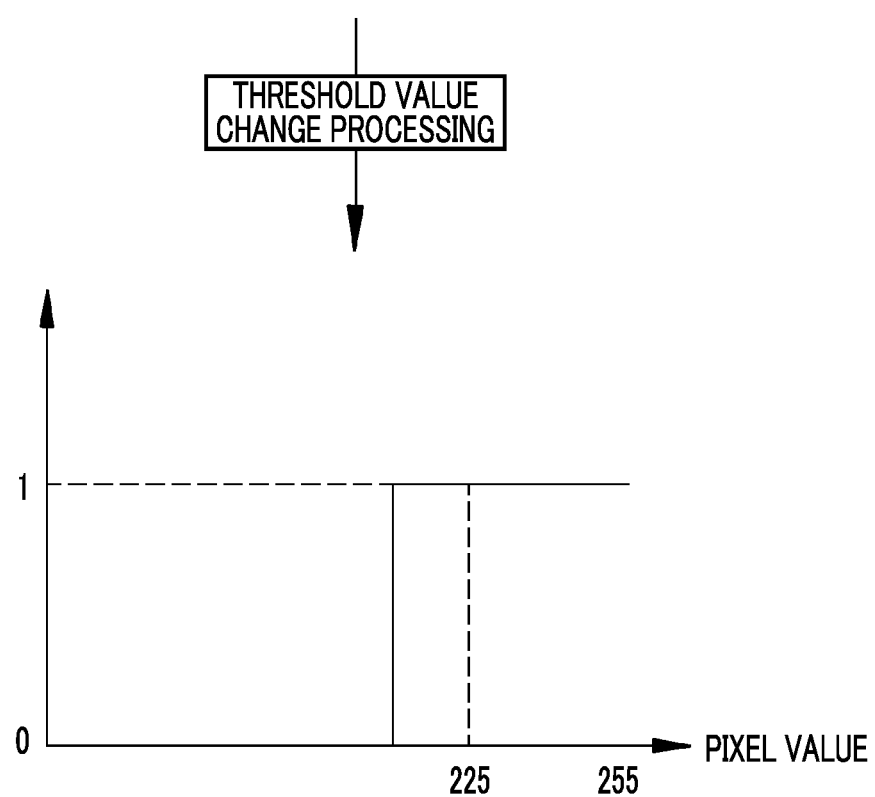

| CRUCIFORM SHAPE WITH GRADATIONS | DISTORTED CRUCIFORM SHAPE | CIRCULAR-AND-CRUCIFORM SHAPE | SHAPE OF MEASUREMENT POINT GROUP |
|---|---|---|---| x (POSITION OF PIXEL OF SPOT IN X DIRECTION)

y (POSITION OF PIXEL OF SPOT IN Y DIRECTION)

x (POSITION OF PIXEL OF SPOT IN X DIRECTION)

y (POSITION OF PIXEL OF SPOT IN Y DIRECTION)

ENDOSCOPE APPARATUS

CROSS-REFERENCE TO RELATED APPLICATIONS

This application is a Continuation of PCT International Application No. PCT/JP2020/001032 filed on 15 Jan. 2020, which claims priority under 35 U.S.C § 119(a) to Japanese Patent Application No. 2019-009946 filed on 24 Jan. 2019. The above application is hereby expressly incorporated by reference, in its entirety, into the present application.

BACKGROUND OF THE INVENTION

1. Field of the Invention

The present invention relates to an endoscope apparatus that measures the size of a subject.

2. Description of the Related Art

A distance to an object to be observed, the size of the object to be observed, and the like are acquired in an endoscope apparatus. In, for example, JP1988-242232A (JP-S63-242232A), a subject is illuminated with illumination light and measurement spotlight and an object to be observed is measured using the position of the spotlight illuminated on the subject. In JP1988-242232A (JP-S63-242232A), a saturation peculiar to the color of the spotlight is extracted to detect the position of the spotlight.

SUMMARY OF THE INVENTION

In a case where auxiliary measurement light, such as measurement spotlight, is used to measure an object to be observed as in JP1988-242232A (JP-S63-242232A), the irradiation position of the auxiliary measurement light on the subject needs to be reliably detected. However, a noise component hindering the detection of the irradiation position of the auxiliary measurement light may be included in a picked-up image that is obtained from the image pickup of the subject illuminated with the auxiliary measurement light and the illumination light. In a case where the noise component is included as described above and, for example, the color of the noise component is substantially the same as the color of the auxiliary measurement light, it may be difficult to detect only the component of the auxiliary measurement light in "the extraction of saturation" disclosed in JP1988-242232A (JP-S63-242232A).

An object of the present invention is to provide an endoscope apparatus that can remove noise components hindering the detection of the irradiation position of auxiliary measurement light used to measure a subject.

An endoscope apparatus according to an embodiment of the present invention comprises an illumination light source unit that emits illumination light used to illuminate a subject, an auxiliary measurement light source unit that emits auxiliary measurement light, and a processor. The processor acquires a picked-up image that is obtained from image pickup of the subject illuminated with the illumination light and the auxiliary measurement light and includes at least two first and second spectral images having different wavelength components, obtains a first arithmetic image from which a first noise component hindering detection of an irradiation position of the auxiliary measurement light is removed by first arithmetic processing based on the first and second spectral images, detects the irradiation position of the auxiliary measurement light from the first arithmetic image, and displays a specific image in which a measurement marker set according to the irradiation position of the auxiliary measurement light is superimposed on the picked-up image.

It is preferable that, in a case where the processor performs first binarization processing of obtaining a binarized first spectral image by binarizing the first spectral image and second binarization processing of obtaining a binarized second spectral image by binarizing the second spectral image, the processor performs first difference processing of the binarized first spectral image and the binarized second spectral image as the first arithmetic processing. It is preferable that the picked-up image includes a third spectral image having a wavelength component different from the wavelength components of the first and second spectral images and the processor obtains a second arithmetic image from which a second noise component different from the first noise component is removed by second arithmetic processing based on the first arithmetic image and the third spectral image. It is preferable that, in a case where the processor performs third binarization processing of obtaining a binarized third spectral image by binarizing the third spectral image, the processor performs second difference processing of the first arithmetic image and the binarized third spectral image as the second arithmetic processing.

It is preferable that the first spectral image is a red image and the second spectral image is a green image. It is preferable that the third spectral image is a red image. It is preferable that a threshold value condition for the first binarization processing is changed by a histogram of the first spectral image and a threshold value condition for the second binarization processing is changed by a histogram of the second spectral image. It is preferable that a threshold value condition for the third binarization processing is changed by a histogram of the third spectral image. It is preferable that the histogram is a histogram of an image, which corresponds to a specific range other than an illumination position-movable range of the auxiliary measurement light, in the picked-up image.

It is preferable that the measurement marker includes a first measurement marker showing an actual size of the subject or a second measurement marker consisting of a crossing line formed on the subject by the auxiliary measurement light and gradations formed on the crossing line and serving as an index of a size of the subject.

According to the present invention, it is possible to remove noise components hindering the detection of the irradiation position of auxiliary measurement light used to measure a subject.

BRIEF DESCRIPTION OF THE DRAWINGS

FIG. 11 is a diagram illustrating threshold value change processing.

DESCRIPTION OF THE PREFERRED EMBODIMENTS

Figure 1:
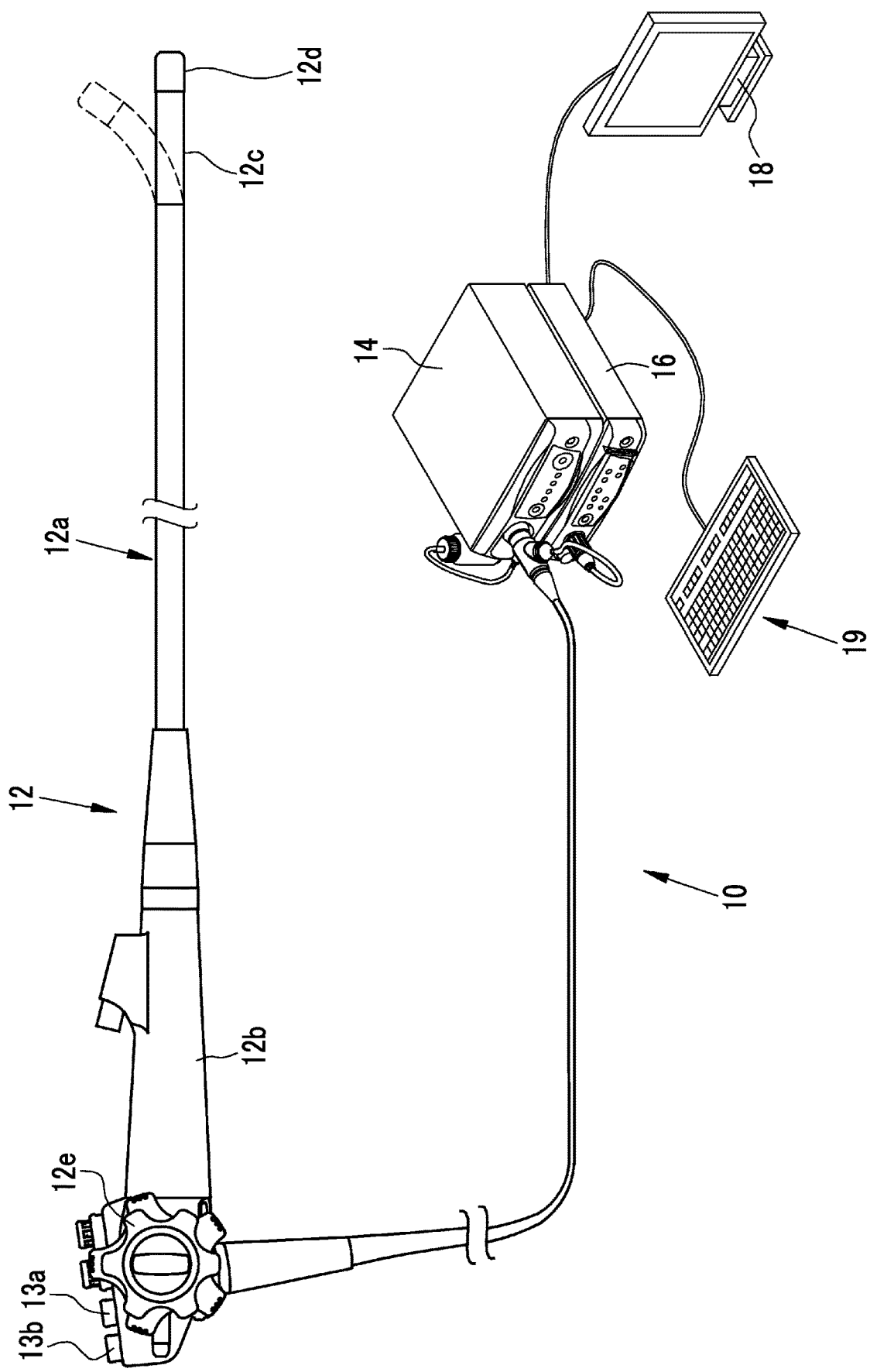
FIG. 1 is a diagram showing the appearance of an endoscope apparatus.

As shown in FIG. 1, an endoscope apparatus 10 includes an endoscope 12, a light source device 14, a processor device 16, a monitor 18, and a user interface 19. The endoscope 12 is optically connected to the light source device 14, and is electrically connected to the processor device 16. The processor device 16 is electrically connected to the monitor 18 (display unit) that displays an image. The user interface 19 is connected to the processor device 16, and is used for various setting operations and the like for the processor device 16. The user interface 19 includes a mouse and the like (not shown) in addition to a keyboard.

The endoscope 12 includes an insertion part 12a that is to be inserted into an object to be examined, an operation part 12b that is provided at the proximal end portion of the insertion part 12a, and a bendable part 12c and a distal end part 12d that are provided on the distal end side of the insertion part 12a. The bendable part 12c operates to be bent by the operation of angle knobs 12e of the operation part 12b. The distal end part 12d is made to face in a desired direction by the bending operation of the bendable part 12c.

The endoscope 12 has a normal light observation mode and a length measurement mode, and these two modes are switched by a mode changeover switch 13a that is provided on the operation part 12b of the endoscope 12. The normal light observation mode is a mode where an object to be observed is illuminated with illumination light. In the length measurement mode, an object to be observed is illuminated with illumination light and auxiliary measurement light and a measurement marker to be used to measure the size of the object to be observed or the like is displayed in a picked-up image obtained from the image pickup of the object to be observed. Auxiliary measurement light is light that is used to measure a subject.

Further, the operation part 12b of the endoscope 12 is provided with a freeze switch 13b that is used to give a static image-acquisition instruction to acquire the static image of a picked-up image. In a case where a user operates the freeze switch 13b, the screen of the monitor 18 is frozen and displayed and an alert sound (for example, "beep") informing the acquisition of a static image is generated together. Then, the static images of the picked-up image, which are obtained before and after the operation timing of the freeze switch 13b, are stored in a static image storage unit 37 (see FIG. 3) provided in the processor device 16. Furthermore, it is preferable that measurement information to be described later is also stored together with the static image of the picked-up image in a case where the endoscope 12 is set to the length measurement mode. The static image storage unit 37 is a storage unit, such as a hard disk or a universal serial bus (USB) memory. In a case where the processor device 16 can be connected to a network, the static image of the picked-up image may be stored in a static image storage server (not shown), which is connected to a network, instead of or in addition to the static image storage unit 37.

A static image-acquisition instruction may be given using an operation device other than the freeze switch 13b. For example, a foot pedal may be connected to the processor device 16, and a static image-acquisition instruction may be given in a case where a user operates the foot pedal (not shown) with a foot. A static image-acquisition instruction may be given by a foot pedal that is used to switch a mode. Further, a gesture recognition unit (not shown), which recognizes the gestures of a user, may be connected to the processor device 16, and a static image-acquisition instruction may be given in a case where the gesture recognition unit recognizes a specific gesture of a user. The gesture recognition unit may also be used to switch a mode.

Furthermore, a sight line input unit (not shown), which is provided close to the monitor 18, may be connected to the processor device 16, and a static image-acquisition instruction may be given in a case where the sight line input unit recognizes that a user's sight line is in a predetermined region of the monitor 18 for a predetermined time or longer. Further, a voice recognition unit (not shown) may be connected to the processor device 16, and a static image-acquisition instruction may be given in a case where the voice recognition unit recognizes a specific voice generated by a user. The voice recognition unit may also be used to switch a mode. Furthermore, an operation panel (not shown), such as a touch panel, may be connected to the processor device 16, and a static image-acquisition instruction may be given in a case where a user makes a specific operation on the operation panel. The operation panel may also be used to switch a mode.

Figure 2:
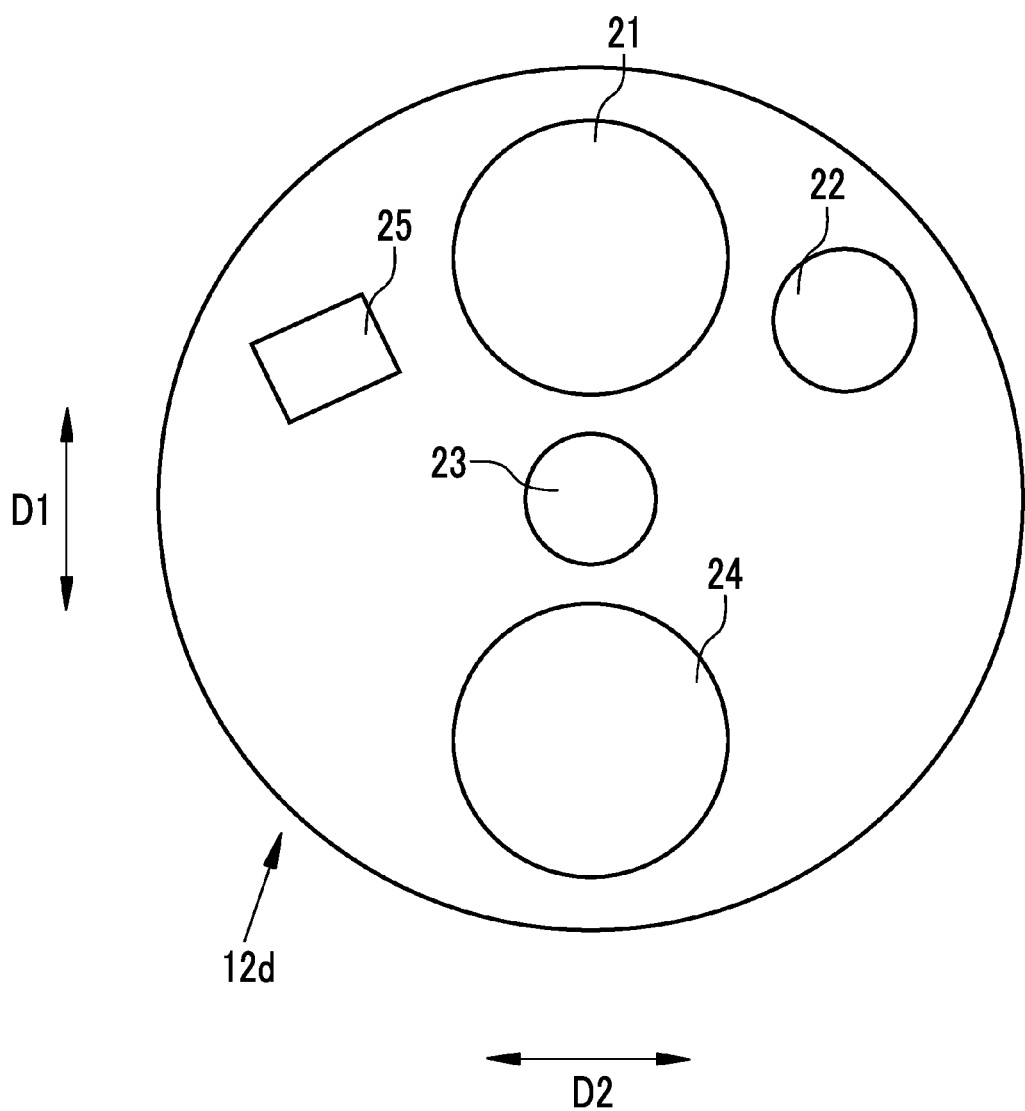
FIG. 2 is a plan view of a distal end part of an endoscope.

As shown in FIG. 2, the distal end part of the endoscope 12 has a substantially circular shape; and is provided with an objective lens 21 that is positioned closest to a subject among optical members of an image pickup optical system of the endoscope 12, an illumination lens 22 that is used to irradiate a subject with illumination light, an auxiliary measurement lens 23 that is used to illuminate a subject with auxiliary measurement light to be described later, an opening 24 that allows a treatment tool to protrude toward a subject, and an air/water supply nozzle 25 that is used to supply air and water.

An optical axis Ax of the objective lens 21 extends in a direction perpendicular to the plane of paper. A vertical first direction D1 is orthogonal to the optical axis Ax, and a horizontal second direction D2 is orthogonal to the optical axis Ax and the first direction D1. The objective lens 21 and the auxiliary measurement lens 23 are arranged in the first direction D1.

Figure 3:
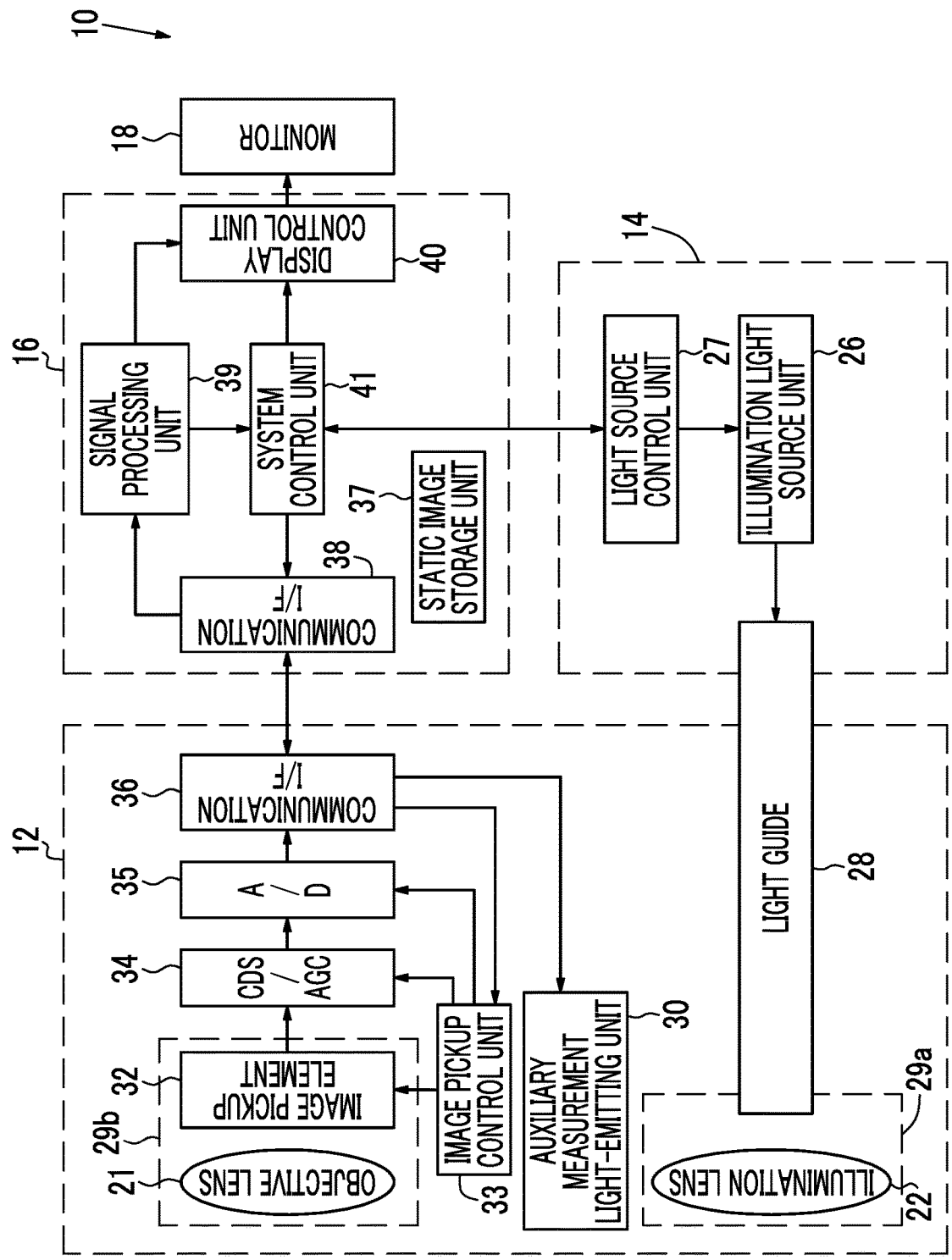
FIG. 3 is a block diagram showing the functions of the endoscope apparatus.

As shown in FIG. 3, the light source device 14 comprises an illumination light source unit 26 and a light source control unit 27. The illumination light source unit 26 generates illumination light that is used to illuminate a subject. Illumination light emitted from the illumination light source unit 26 is incident on a light guide 28, and a subject is irradiated with illumination light through the illumination lens 22. In the illumination light source unit 26, a white light source emitting white light, a plurality of light sources, which includes a white light source and a light source emitting another color light (for example, a blue light source emitting blue light), or the like is used as a light source of illumination light. The light source control unit 27 is connected to a system control unit 41 of the processor device 16. Mixed white light, which is a combination of blue light, green light, and red light, may be used as illumination light. In this case, it is preferable that the illumination lens 22 is optically designed to allow the irradiation range of green light to be wider than the irradiation range of red light.

The light source control unit 27 controls the illumination light source unit 26 on the basis of an instruction given from the system control unit 41. The system control unit 41 not only instructs the light source control unit 27 to control a light source but also controls a light source 30a (see FIG. 4) of an auxiliary measurement light-emitting unit 30. In the normal light observation mode, the system control unit 41 performs control to turn on illumination light and to turn off auxiliary measurement light. In the length measurement mode, the system control unit 41 performs control to turn on illumination light and to turn on auxiliary measurement light.

An illumination optical system 29a, an image pickup optical system 29b, and an auxiliary measurement light-emitting unit 30 are provided in the distal end part 12d of the endoscope 12. The illumination optical system 29a includes the illumination lens 22, and an object to be observed is irradiated with light, which is emitted from the light guide 28, through the illumination lens 22. The image pickup optical system 29b includes the objective lens 21 and an image pickup element 32. Light reflected from the object to be observed is incident on the image pickup element 32 through the objective lens 21. Accordingly, the reflected image of the object to be observed is formed on the image pickup element 32.

The image pickup element 32 is a color image pickup sensor, and picks up the reflected image of an object to be examined and outputs image signals. It is preferable that the image pickup element 32 is a charge coupled device (CCD) image pickup sensor, a complementary metal-oxide semiconductor (CMOS) image pickup sensor, or the like. The image pickup element 32 used in an embodiment of the present invention is a color image pickup sensor that is used to obtain red images, green images, and blue images having three colors of R (red), G (green), and B (blue). The red images are images that are output from red pixels provided with red color filters in the image pickup element 32. The green images are images that are output from green pixels provided with green color filters in the image pickup element 32. The blue images are images that are output from blue pixels provided with blue color filters in the image pickup element 32. The image pickup element 32 is controlled by an image pickup control unit 33.

Image signals output from the image pickup element 32 are transmitted to a CDS/AGC circuit 34. The CDS/AGC circuit 34 performs correlated double sampling (CDS) or auto gain control (AGC) on the image signals that are analog signals. The image signals, which have been transmitted through the CDS/AGC circuit 34, are converted into digital image signals by an analog/digital converter (A/D converter) 35. The digital image signals, which have been subjected to A/D conversion, are input to the processor device 16 through a communication interface (I/F) 36.

In the processor device 16, various programs used to perform various kinds of processing or functions are stored in a program memory. Various programs are operated by the system control unit 41 formed of a processor, so that the processor device 16 realizes the functions of a communication interface (I/F) 38 (image acquisition unit) connected to the communication I/F 36 of the endoscope 12, a signal processing unit 39, and a display control unit 40. Accordingly, the functions of a first signal processing section 50 and a second signal processing section included in the signal processing unit 39 are realized. Further, the functions of a mask processing section 53, a binarization processing section 54, a noise component-removal section 56, and an irradiation position-detection section 58 included in the first signal processing section 50 are realized.

The communication I/F receives the image signals, which are transmitted from the communication I/F 36 of the endoscope 12, and transmits the image signals to the signal processing unit 39. A memory, which temporarily stores the image signals received from the communication I/F 38, is built in the signal processing unit 39, and the signal processing unit 39 processes an image signal group, which is a set of the image signals stored in the memory, to generate the picked-up image. In a case where the endoscope 12 is set to the length measurement mode, the signal processing unit 39 may be adapted to perform structure-emphasis processing of emphasizing structures, such as blood vessels, or color difference-emphasis processing of increasing a color difference between a normal area and a lesion area of the object to be observed on the picked-up image.

The display control unit 40 causes the monitor 18 to display the picked-up image that is generated by the signal processing unit 39. The system control unit 41 performs the control of the image pickup element 32 through the image pickup control unit 33 provided in the endoscope 12. The image pickup control unit 33 also performs the control of the CDS/AGC circuit 34 and the A/D converter 35 together with the control of the image pickup element 32.

Figure 4:
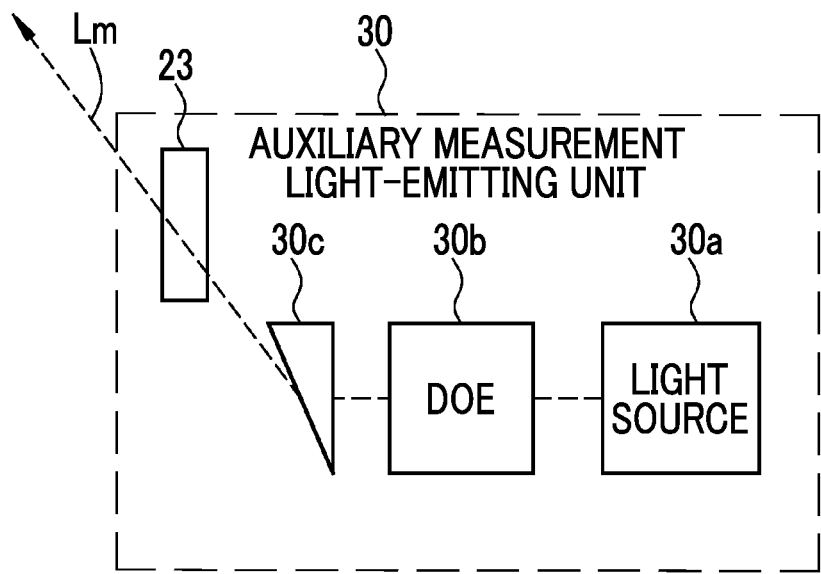
FIG. 4 is a block diagram of an auxiliary measurement light-emitting unit.

As shown in FIG. 4, the auxiliary measurement light-emitting unit 30 (auxiliary measurement light source unit) comprises a light source 30a, a diffractive optical element (DOE) 30b, a prism 30c, and the auxiliary measurement lens 23. The light source 30a is to emit light having a color that can be detected by pixels of the image pickup element 32 (specifically visible light), and includes a light-emitting element, such as a laser light source LD (laser diode) or a light emitting diode (LED), and a condenser lens that condenses light emitted from the light-emitting element.

Red laser light having a wavelength in the range of, for example, 600 nm to 650 nm is used in this embodiment as light that is emitted from the light source 30a. However, light having a wavelength in other ranges, for example, green light having a wavelength in the range of, for example, 495 nm to 570 nm may be used. It is preferable that the red laser light has high directivity. Further, it is preferable that the central portion of a region irradiated with the red laser light is illuminated with a large amount of light that is enough to cause halation (pixel saturation) in the image pickup element 32. The light source 30a is controlled by the system control unit 41 and emits light on the basis of an instruction given from the system control unit 41. The DOE 30b converts the light, which is emitted from the light source, into auxiliary measurement light that is used to obtain measurement information.

A blue laser light source or a green laser light source may be used as the laser light source in addition to a red laser light source, but it is preferable that a red laser light source is used since a blue laser light source or a green laser light source requires high cost for a user at the time of introduction and maintenance. However, red laser light may be mixed with a red color caused by a human body in the case of a red laser light source, but this problem can be solved since the red color caused by a human body can be removed by processing of removing noise components to be described later and only red laser light, which is auxiliary measurement light, can be extracted.

Figure 5:
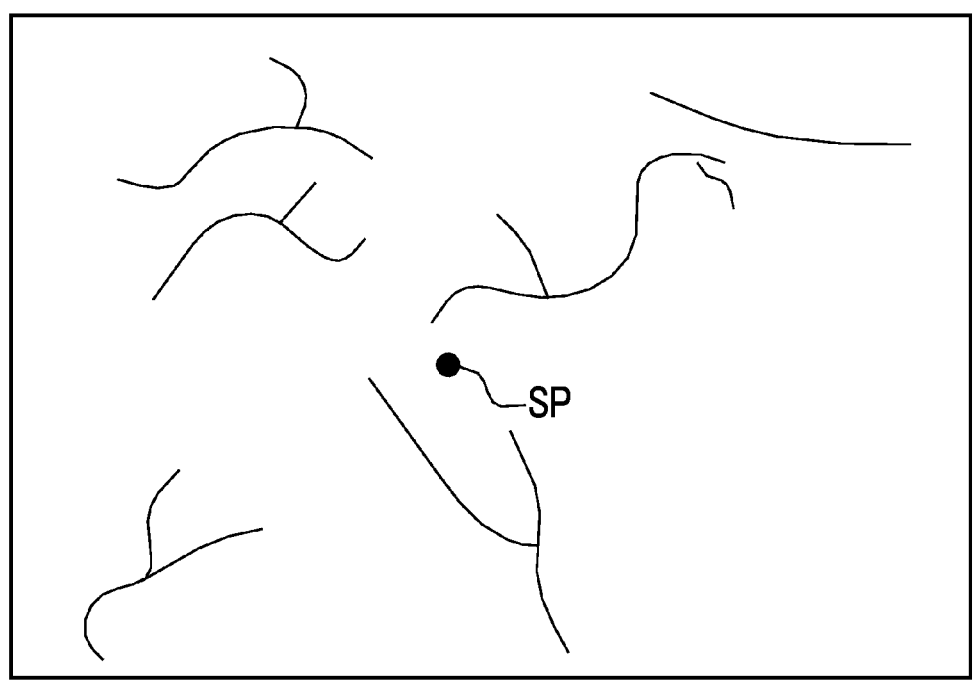
FIG. 5 is a diagram illustrating a spot SP that is formed on a subject by auxiliary measurement light.

The prism 30c is an optical member that is used to change the travel direction of auxiliary measurement light converted by the DOE 30b. The prism 30c changes the travel direction of auxiliary measurement light so that the auxiliary measurement light crosses the visual field of the image pickup optical system including the objective lens 21 and lens groups. The details of the travel direction of auxiliary measurement light will also be described later. A subject is irradiated with auxiliary measurement light Lm, which is emitted from the prism 30c, through the auxiliary measurement lens 23. In a case where the subject is irradiated with the auxiliary measurement light, a spot SP as a circular region is formed on the subject as shown in FIG. 5. The position of the spot SP (the irradiation position of the auxiliary measurement light) is detected by the irradiation position-detection section 58 (see FIG. 7), and a measurement marker showing an actual size is set according to the position of the spot SP. The set measurement marker is displayed in the picked-up image. Plural kinds of measurement markers, such as a first measurement marker and a second measurement marker, are included in the measurement marker as described later, and a measurement marker to be displayed in the picked-up image among the plural kinds of measurement markers can be selected according to a user's instruction. For example, the user interface 19 is used for the user's instruction.

An auxiliary measurement slit formed in the distal end part 12d of the endoscope may be used instead of the auxiliary measurement lens 23. Further, it is preferable that an anti-reflection coating (AR coating) (anti-reflection portion) is provided on the auxiliary measurement lens 23. The reason why the anti-reflection coating is provided as described above is that it is difficult for the irradiation position-detection section 58 to be described later to recognize the position of the spot SP formed on the subject by auxiliary measurement light in a case where the auxiliary measurement light is reflected without being transmitted through the auxiliary measurement lens 23 and a ratio of the auxiliary measurement light with which a subject is irradiated is reduced.

The auxiliary measurement light-emitting unit 30 has only to be capable of emitting auxiliary measurement light to the visual field of the image pickup optical system. For example, the light source 30a may be provided in the light source device and light emitted from the light source 30a may be guided to the DOE 30b by optical fibers. Further, the prism 30c may not be used and the directions of the light source 30a and the DOE 30b may be inclined with respect to the optical axis Ax so that auxiliary measurement light Lm is emitted in a direction crossing the visual field of the image pickup optical system.

Figure 6:
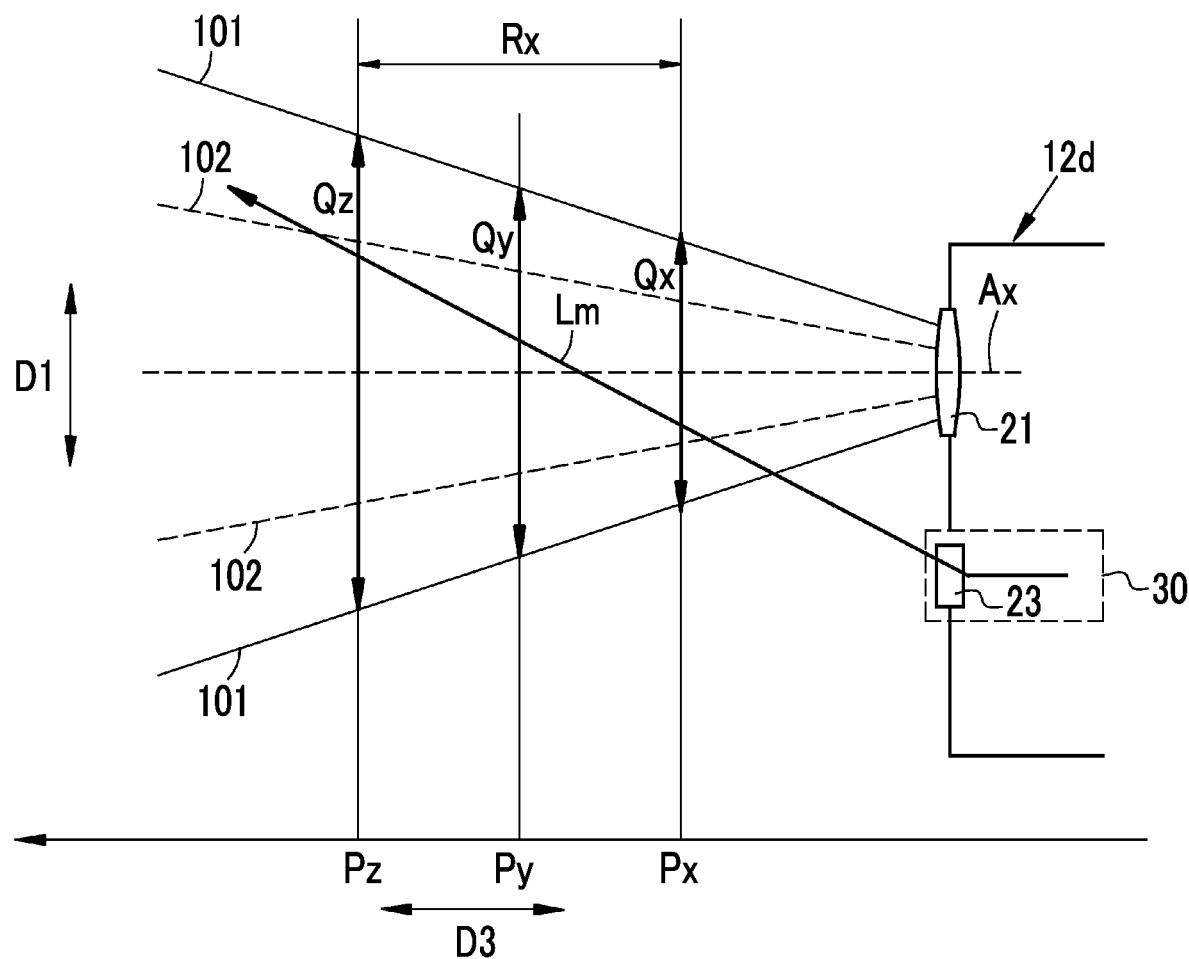
FIG. 6 is a diagram illustrating a relationship between the distal end part of the endoscope and a near end Px, an intermediate vicinity Py, and a far end Pz in a range Rx of an observation distance.

With regard to the travel direction of auxiliary measurement light, auxiliary measurement light Lm is emitted in a state where an optical axis Lm of the auxiliary measurement light Lm crosses the optical axis Ax of the objective lens 21 as shown in FIG. 6. In a case where a subject can be observed in a range Rx of an observation distance, it is understood that the positions (points where the respective arrows Qx, Qy, and Qz cross the optical axis Ax) of the spot SP, which is formed on the subject by the auxiliary measurement light Lm, in image pickup ranges (shown by arrows Qx, Qy, and Qz) at a near end Px, an intermediate vicinity Py, and a far end Pz of the range Rx are different from each other. The image pickup angle of view of the image pickup optical system is represented by a region between two solid lines 101, and measurement is performed in a central region (a region between two dotted lines 102), in which an aberration is small, of this image pickup angle of view.

Since the auxiliary measurement light Lm is emitted in a state where the optical axis Lm of the auxiliary measurement light crosses the optical axis Ax as described above, sensitivity to the movement of the position of the spot with respect to a change in the observation distance is high. Accordingly, the size of the subject can be measured with high accuracy. Then, the image of the subject illuminated with the auxiliary measurement light is picked up by the image pickup element 32, so that a picked-up image including the spot SP is obtained. In the picked-up image, the position of the spot SP varies depending on a relationship between the optical axis Ax of the objective lens 21 and the optical axis Lm of the auxiliary measurement light Lm and an observation distance. However, the number of pixels showing the same actual size (for example, 5 mm) is increased in the case of a short observation distance, and the number of pixels showing the same actual size (for example, 5 mm) is reduced in the case of a long observation distance.

Accordingly, in a case where information showing a relationship between the position of the spot SP and measurement information (the number of pixels) corresponding to the actual size of a subject is stored in advance as described in detail later, the measurement information can be calculated from the position of the spot SP.

Figure 7:
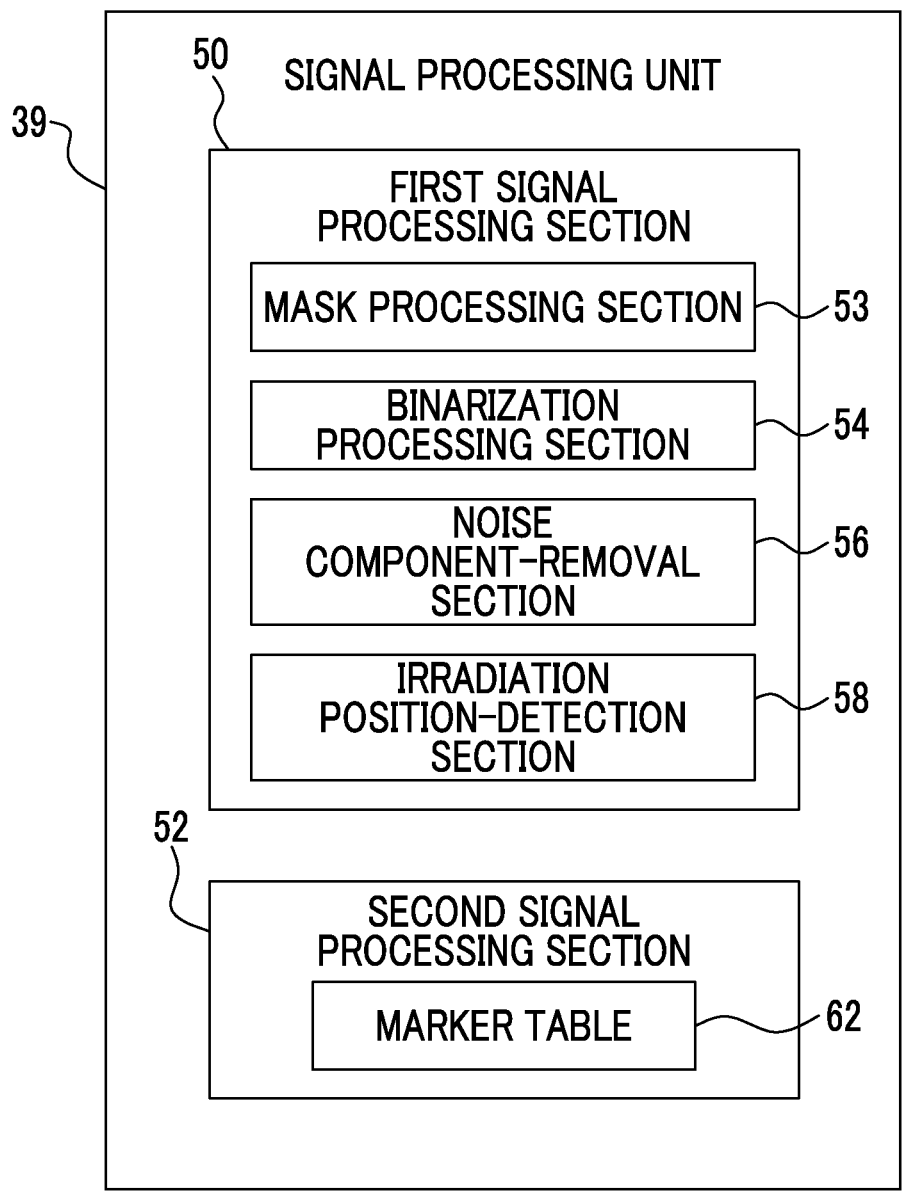
FIG. 7 is a block diagram showing the functions of a signal processing unit.
Figure 8:
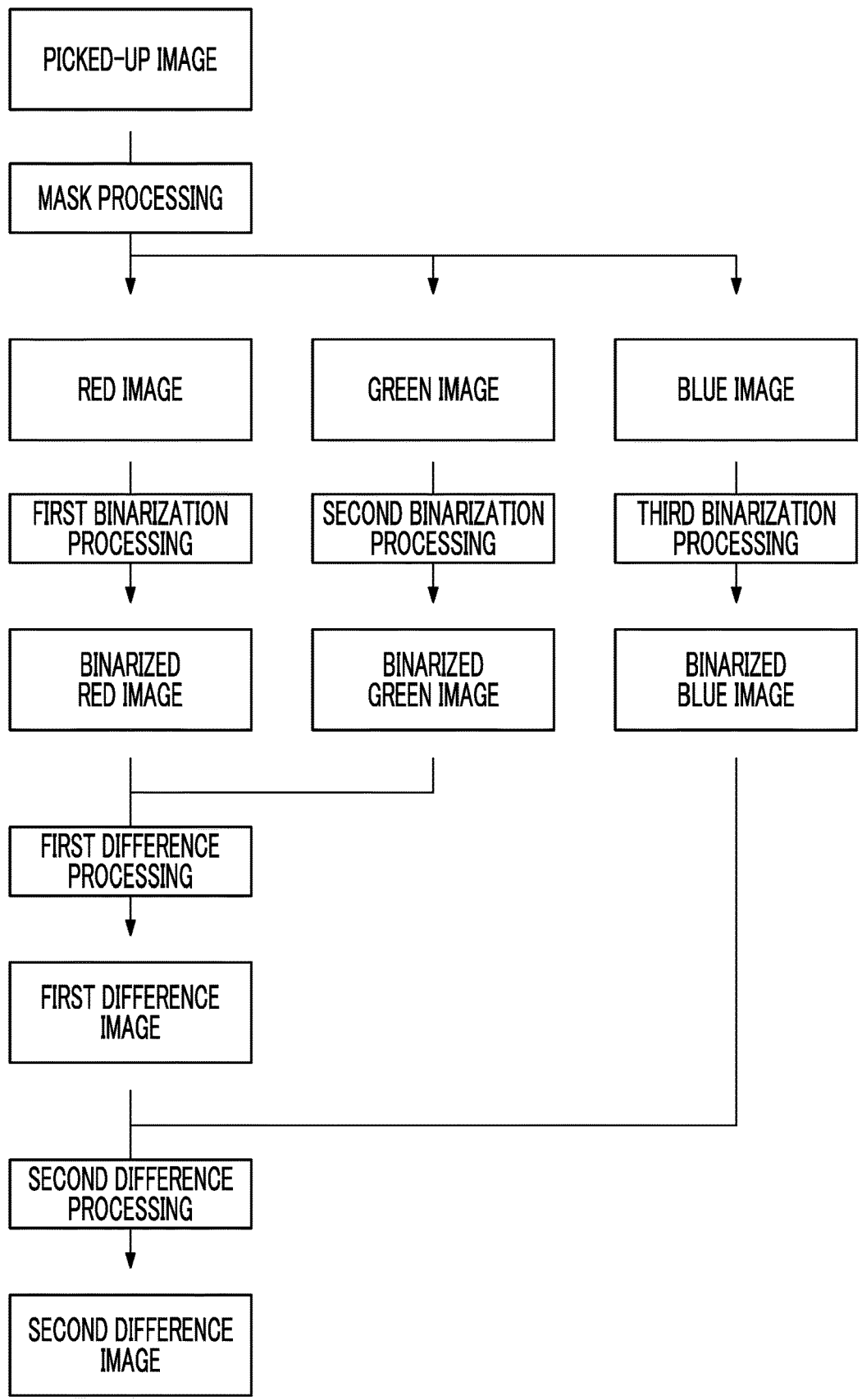
FIG. 8 is a block diagram showing processing of removing noise.

As shown in FIG. 7, the signal processing unit 39 of the processor device 16 comprises a first signal processing section 50 and a second signal processing section 52 to recognize the position of the spot SP and to set a measurement marker. The first signal processing section 50 detects the position of the spot SP in the picked-up image, and the second signal processing section 52 sets a measurement marker according to the position of the spot SP. A specific image is caused to be displayed on the monitor 18 by the display control unit 40. In a case where the endoscope 12 is set to the normal light observation mode, the picked-up image of a subject illuminated with illumination light is input to the signal processing unit 39. In a case where the endoscope 12 is set to the length measurement mode, the picked-up image of the subject illuminated with illumination light and auxiliary measurement light is input to the signal processing unit 39. The picked-up image is acquired by the communication I/F 38 (image acquisition unit) connected to the endoscope 12.

Figure 9:
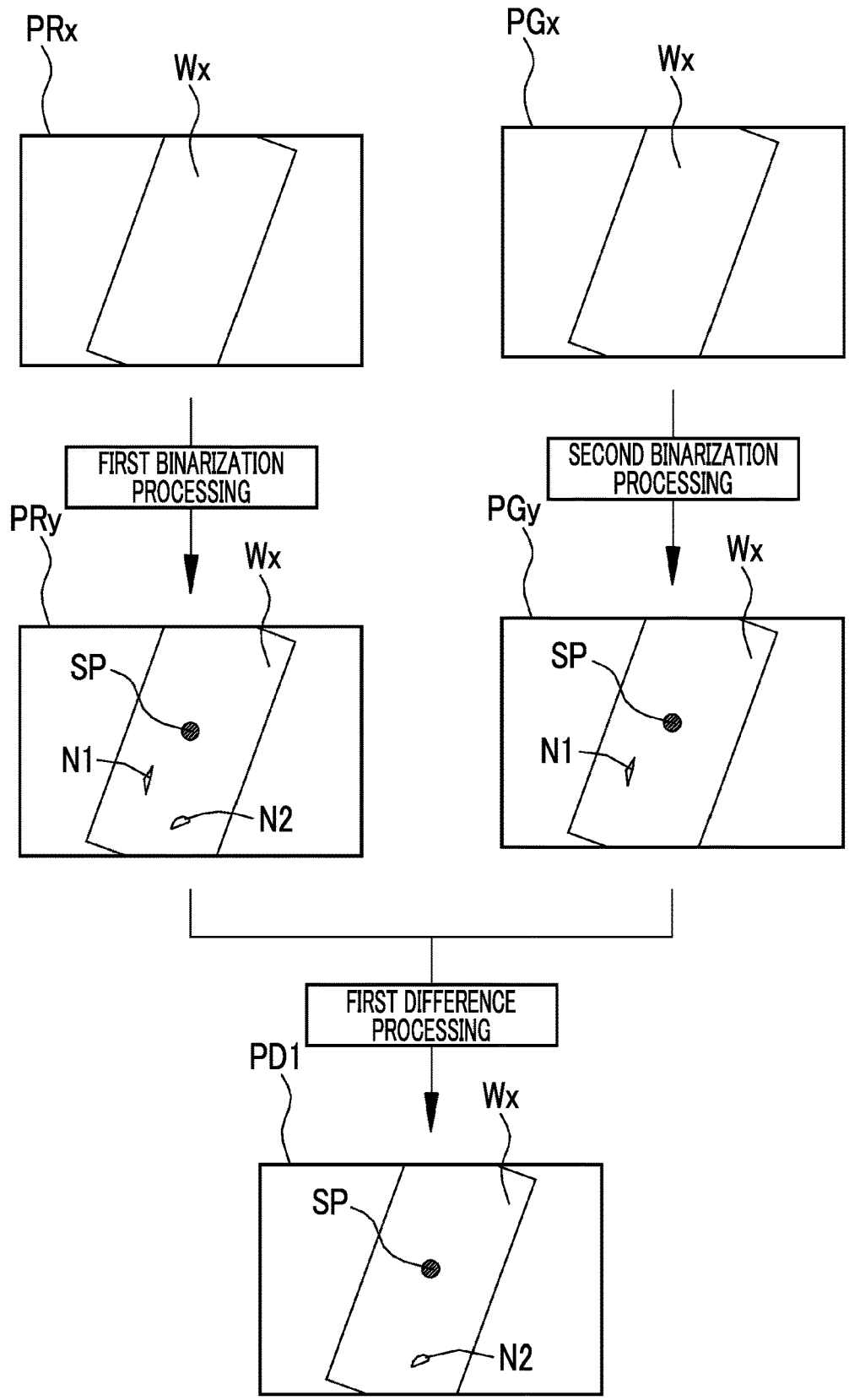
FIG. 9 is a diagram illustrating first binarization processing, second binarization processing, and first difference processing.
Figure 10:
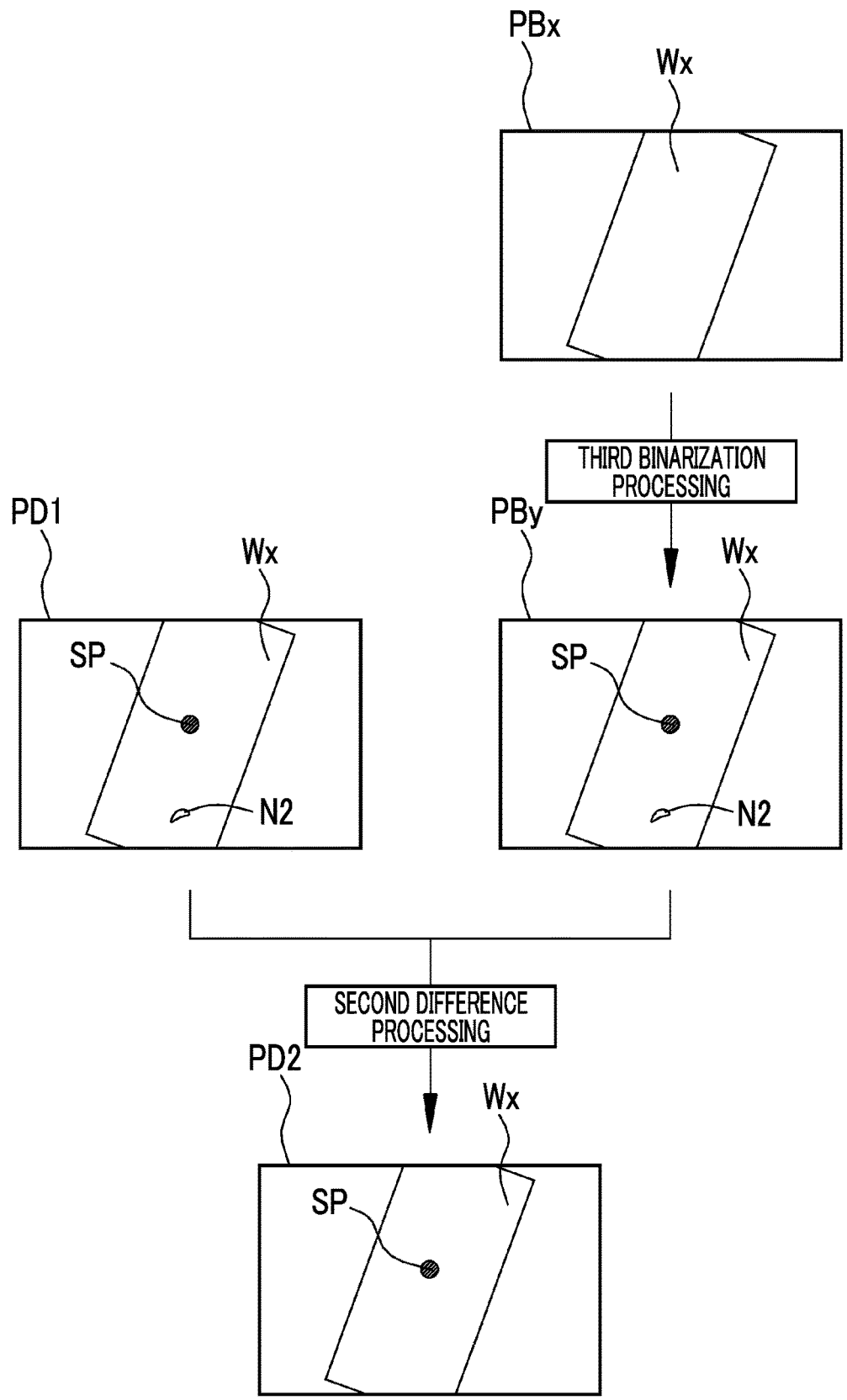
FIG. 10 is a diagram illustrating third binarization processing and second difference processing.

The first signal processing section 50 comprises the mask processing section 53, the binarization processing section 54, the noise component-removal section 56, and the irradiation position-detection section 58. Processing of removing noise components in the first signal processing section 50 will be described with reference to FIGS. 8 to 11. The mask processing section 53 performs mask processing of extracting a substantially parallelogram-shaped illumination position-movable range Wx, which represents the movable range of the illumination position of the auxiliary measurement light on the subject, on a red image (first spectral image), a green image (second spectral image), and a blue image (third spectral image) of the picked-up image. Accordingly, a red image PRx, a green image PGx, and a blue image PBx from which the illumination position-movable ranges Wx have been extracted and which have been subjected to the mask processing are obtained as shown in FIGS. 9 and 10. Noise components are removed from pixels present in the illumination position-movable ranges, and the irradiation position of the spot SP is detected.

Next, the binarization processing section 54 obtains a binarized red image PRy (binarized first spectral image) by performing first binarization processing on pixels present in the illumination position-movable range in the red image PRx having been subjected to the mask processing. In the first binarization processing, as shown in FIG. 9, as a threshold value condition for the first binarization processing, pixels having a pixel value of "225" or more are defined as "1" and pixels having a pixel value less than "225" are defined as "0". The spot SP, which is a component of the auxiliary measurement light, is detected by this first binarization processing. However, in the first binarization processing, a second noise component N2, which is halation (pixel saturation) caused by illumination light, is also detected in addition to a first noise component N1 that is a high-brightness component of a red component of the illumination light. These first and second noise components are factors that hinder the detection of the irradiation position of the spot SP. The threshold value condition refers to a condition that defines the range of the pixel value of a pixel defined as "0" by binarization and the range of the pixel value of a pixel defined as "1" by binarization in addition to a condition that is related to a threshold value indicating a boundary between the pixel value of a pixel defined as "0" by binarization and the pixel value of a pixel defined as "1" by binarization.

Then, in order to remove the first noise component, the noise component-removal section 56 performs first difference processing (first arithmetic processing) of the binarized red image PRy and a binarized green image PGy (binarized second spectral image) that is the green image PGx binarized by second binarization processing. The first noise component N1 has been removed in a first difference image PD1 (first arithmetic image) that is obtained from the first difference processing. However, the second noise component N2 often remains in the first difference image PD1 without being removed. The pixel value of a pixel, which is defined as "0" or less by the first difference processing, is set to "0". In the second binarization processing, as a threshold value condition for the second binarization processing, pixels having a pixel value in the range of "30" to "220" are defined as "1" and pixels having a pixel value in other ranges, that is, a pixel value equal to or larger than "0" and less than "30" or exceeding "220" are defined as "0". The first noise component is removed by the first difference processing of the binarized red image and the binarized green image, but the first noise component may be removed by other first arithmetic processing.

Further, in order to remove the second noise component, as shown in FIG. 10, the noise component-removal section 56 performs second difference processing (second arithmetic processing) of the first difference image PD1 and a binarized blue image PBy (binarized third spectral image) that is the blue image PBx binarized by third binarization processing. The second noise component, which is difficult to be removed by the first difference processing, has been removed in a second difference image PD2 (second arithmetic image) that is obtained from the second difference processing. The pixel value of a pixel, which is defined as "0" or less by the second difference processing as in the first difference processing, is set to "0". In the third binarization processing, as a threshold value condition for the third binarization processing, pixels having a pixel value equal to or larger than "160" are defined as "1" and pixels having a pixel value less than "160" are defined as "0". The second noise component is removed by the second difference processing of the first difference image and the binarized blue image, but the second noise component may be removed by other second arithmetic processing.

With regard to the threshold value conditions for the first, second, and third binarization processing, there is a case where it is difficult to reliably detect the irradiation position of the spot SP and it is difficult to reliably remove the first and second noise components due to a variation in the sensitivity of the image pickup element 32 of each endoscope 12. Accordingly, it is preferable that threshold value change processing of changing the threshold value conditions for the first, second, and third binarization processing is performed using the histogram of an image of a specific range Wy other than the illumination position-movable range Wx. For example, in the case of the threshold value condition for the first binarization processing, as shown in FIG. 11, pixels having a pixel value of "225" or more are defined as "1" before threshold value change processing based on a histogram but pixels defined as "1" are changed to pixels having a pixel value, which is equal to or larger than a pixel value smaller than, for example, "225", by threshold value change processing based on a histogram of the specific range Wy of a red image. The histogram of an image is a graph showing the frequency distribution of pixel values included in the image, and can show a pixel value on a horizontal axis and show the frequency of a pixel value on a vertical axis in the case of a two-dimensional graph. Further, in the length measurement mode, threshold value change processing different from that of the normal light observation mode may be performed in the case of a special light observation mode in which special light, such as light including light of which a specific wavelength range is narrowed is used.

The irradiation position-detection section 58 detects the irradiation position of the spot SP from the first difference image or the second difference image. It is preferable that the coordinates of the position of the centroid of the spot SP are acquired in the irradiation position-detection section 58 as the irradiation position of the spot SP.

The second signal processing section 52 sets a first measurement marker, which shows the actual size of a subject, as a measurement marker on the basis of the position of the spot SP. The second signal processing section 52 calculates the size of a marker from the position of the spot with reference to a marker table 62 in which a relationship between the position of the spot SP and the first measurement marker showing the actual size of the subject is stored. Then, the second signal processing section 52 sets a first measurement marker corresponding to the size of the marker. In a case where the setting of the first measurement marker is completed, the display control unit 40 causes the monitor 18 to display a specific image in which the first measurement marker is superimposed on a picked-up image obtained from the image pickup of a subject illuminated with illumination light so that the spot SP is positioned at the center of the first measurement marker.

Figure 12:
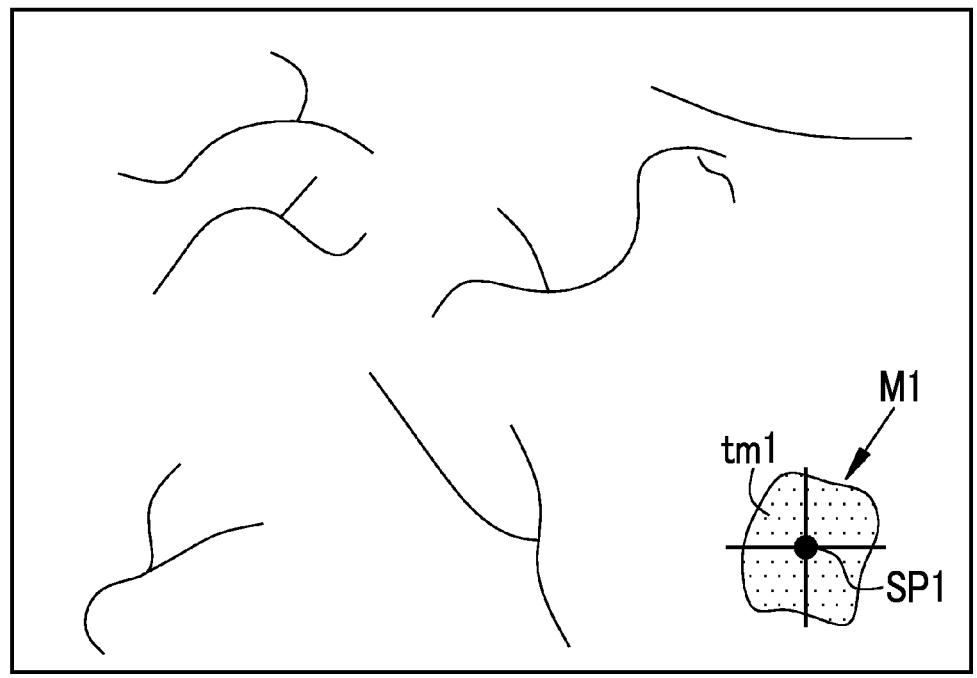
FIG. 12 is an image diagram showing a spot and a first measurement marker in a case where an observation distance corresponds to the near end Px.

For example, a cruciform measurement marker is used as the first measurement marker. In this case, as shown in FIG. 12, a cruciform marker M1, which shows an actual size of 5 mm (a horizontal direction and a vertical direction of the picked-up image), is displayed at the center of a spot SP1 formed on a tumor tm1 of a subject in a case where an observation distance is close to the near end Px. Since the tumor tm1 and a range determined by the cruciform marker M1 substantially coincide with each other, the size of the tumor tm1 can be measured as about 5 mm. The spot is not displayed and only the first measurement marker may be displayed in the picked-up image.

Figure 13:
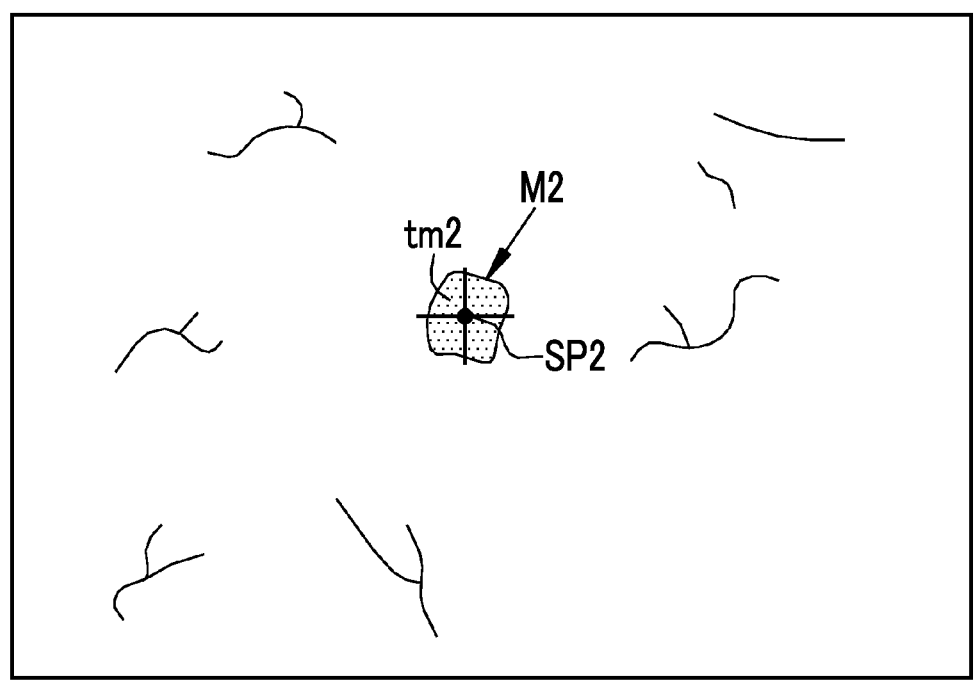
FIG. 13 is an image diagram showing a spot and a first measurement marker in a case where an observation distance corresponds to the intermediate vicinity Py.
Figures 14, 15:
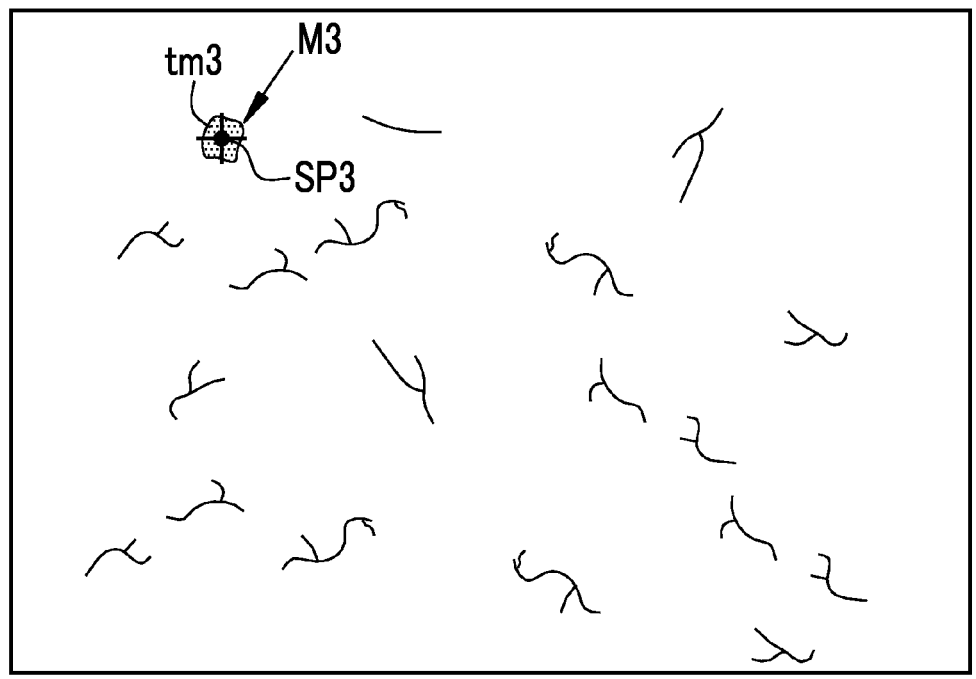
FIG. 14 is an image diagram showing a spot and a first measurement marker in a case where an observation distance corresponds to the far end Pz.
FIG. 15 is a diagram illustrating first measurement markers having a cruciform shape with gradations, a distorted cruciform shape, a circular-and-cruciform shape, and the shape of a measurement point group.

Likewise, as shown in FIG. 13, a cruciform marker M2, which shows an actual size of 5 mm (the horizontal direction and the vertical direction of the picked-up image), is displayed at the center of a spot SP2 formed on a tumor tm2 of a subject in a case where an observation distance is close to the intermediate vicinity Py. Further, as shown in FIG. 14, a cruciform marker M3, which shows an actual size of 5 mm (the horizontal direction and the vertical direction of the picked-up image), is displayed at the center of a spot SP3 formed on a tumor tm3 of a subject. Since the position of the spot on the image pickup surface of the image pickup element 32 varies depending on an observation distance as described above, a position where the marker is displayed also varies. As shown in FIGS. 12 to 14 having been described above, the size of the first measurement marker corresponding to the same actual size of 5 mm is reduced with an increase in an observation distance.

In FIGS. 12 to 14, the center of the spot SP and the center of the marker are displayed to coincide with each other. However, the first measurement marker may be displayed at a position away from the spot SP in a case where there is no problem in measurement accuracy. Even in this case, it is preferable that the first measurement marker is displayed near the spot. Furthermore, the distorted first measurement marker is not displayed, and the distortion of the picked-up image may be corrected so that an undistorted first measurement marker may be displayed in a corrected picked-up image.

Further, the first measurement marker corresponding to the actual size of the subject, which is 5 mm, is displayed in FIGS. 12 to 14, but the actual size of the subject may be set to any value (for example, 2 mm, 3 mm, 10 mm, or the like) according to an object to be observed or the purpose of observation. Furthermore, the first measurement marker has a cruciform shape where a vertical line and a horizontal line are orthogonal to each other in FIGS. 12 to 14, but may have a cruciform shape with gradations where gradations Mx are given to at least one of a vertical line or a horizontal line of a cruciform shape as shown in FIG. 15. Further, the first measurement marker may have a distorted cruciform shape of which at least one of a vertical line or a horizontal line is inclined. Furthermore, the first measurement marker may have a circular-and-cruciform shape where a cruciform shape and a circle are combined with each other. In addition, the first measurement marker may have the shape of a measurement point group where a plurality of measurement points EP corresponding to an actual size from a spot are combined with each other. Further, one first measurement marker may be displayed or a plurality of first measurement markers may be displayed, and the color of the first measurement marker may be changed according to an actual size.

A method of creating the marker table 62 will be described below. A relationship between the position of a spot and the size of a marker can be obtained from image pickup of a chart in which a pattern having an actual size is regularly formed. For example, auxiliary measurement light having the shape of a spot is emitted to a chart, and the image of a graph paper-shaped chart including ruled lines having an interval (5 mm) equal to an actual size or ruled lines having an interval (for example, 1 mm) smaller than the actual size is picked up while an observation distance is changed to change the position of the spot. As a result, a relationship between the position of the spot (the coordinates of a pixel on the image pickup surface of the image pickup element 32) and the number of pixels corresponding to the actual size (the number of pixels representing an actual size of 5 mm) is acquired.

Figure 16:
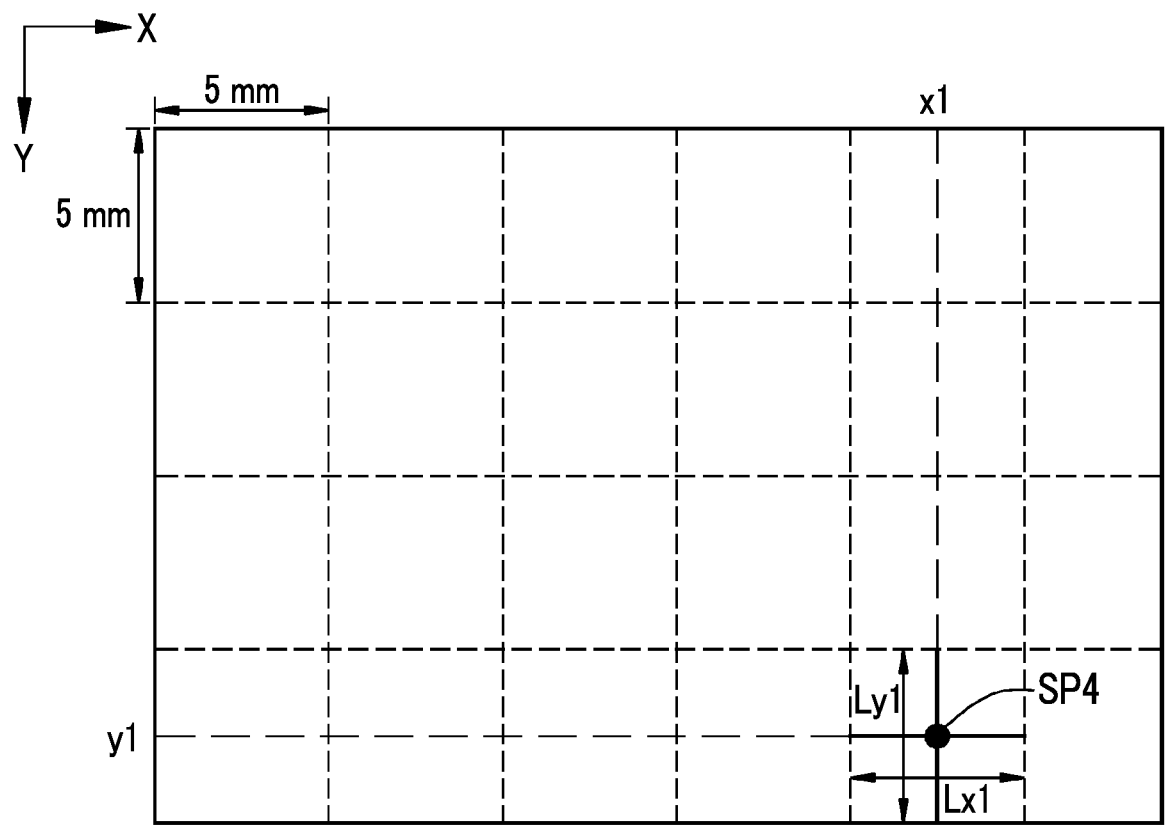
FIG. 16 is a diagram illustrating a graph paper-shaped chart that is used to measure a relationship between the position of a spot and the size of a first measurement marker in a case where an observation distance corresponds to the near end Px.
Figure 17:
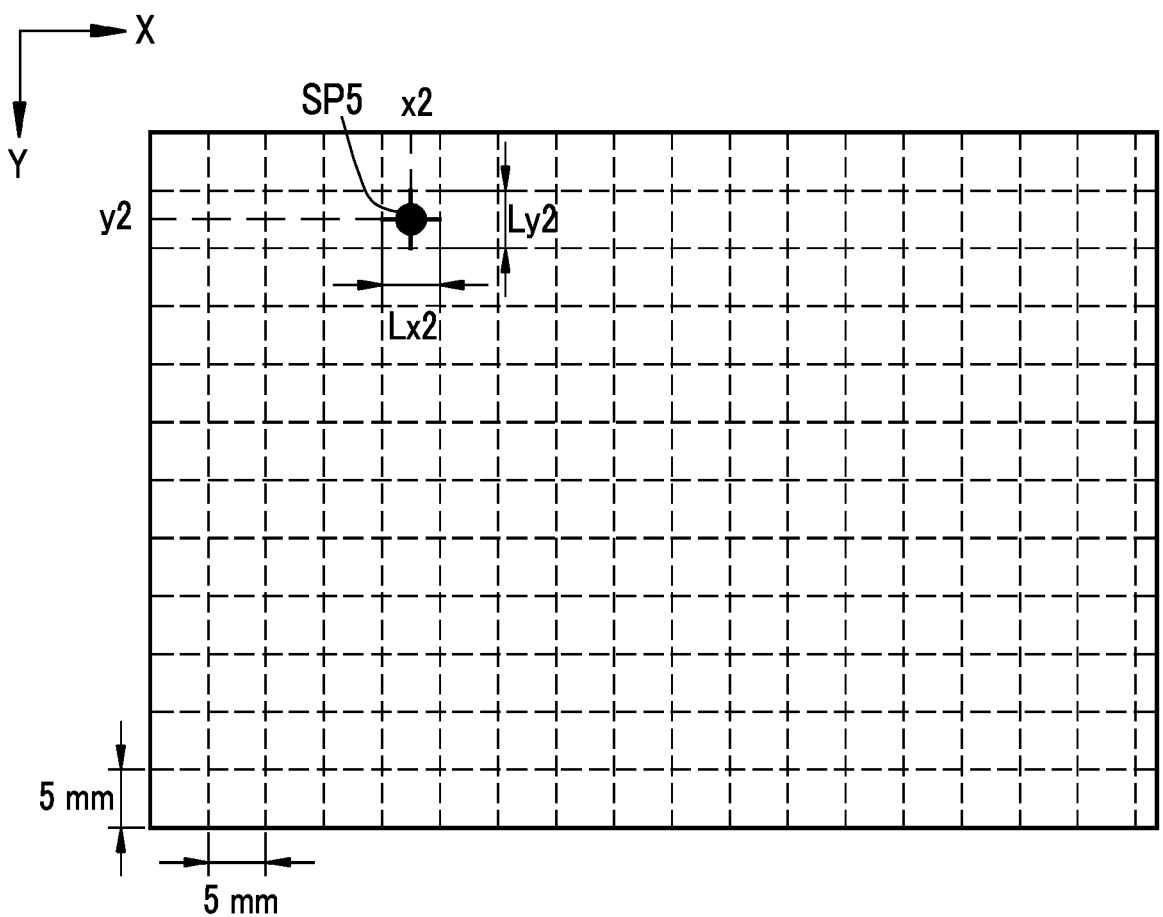
FIG. 17 is a diagram illustrating a graph paper-shaped chart that is used to measure a relationship between the position of a spot and the size of a first measurement marker in a case where an observation distance corresponds to the far end Py.

As shown in FIG. 16, (x1,y1) is the position of a pixel of a spot SP4 in the X and Y directions on the image pickup surface of the image pickup element 32 (an upper left point is the origin of a coordinate system). The number of pixels in the X direction corresponding to an actual size of 5 mm at the position (x1,y1) of the spot SP4 is denoted by Lx1, and the number of the pixels in the Y direction corresponding to the actual size at the position is denoted by Ly1. Such a measurement is repeated while an observation distance is changed. FIG. 17 shows a state where the image of a chart including ruled lines having the same interval, which is 5 mm, as that in FIG. 16 is picked up, but is a state where an observation distance is closer to the far end than in the state shown in FIG. 16 and an interval between the ruled lines is displayed so as to be narrower. In the state shown in FIG. 17, the number of pixels in the X direction corresponding to an actual size of 5 mm at the position (x2,y2) of a spot SP5 on the image pickup surface of the image pickup element 32 is denoted by Lx2, and the number of the pixels in the Y direction corresponding to the actual size at the position is denoted by Ly2. Further, measurement shown in FIGS. 16 and 17 is repeated while an observation distance is changed; and results thereof are plotted. The chart is shown in FIGS. 16 and 17 without the consideration of the distortion of the objective lens 21.

Figure 18:
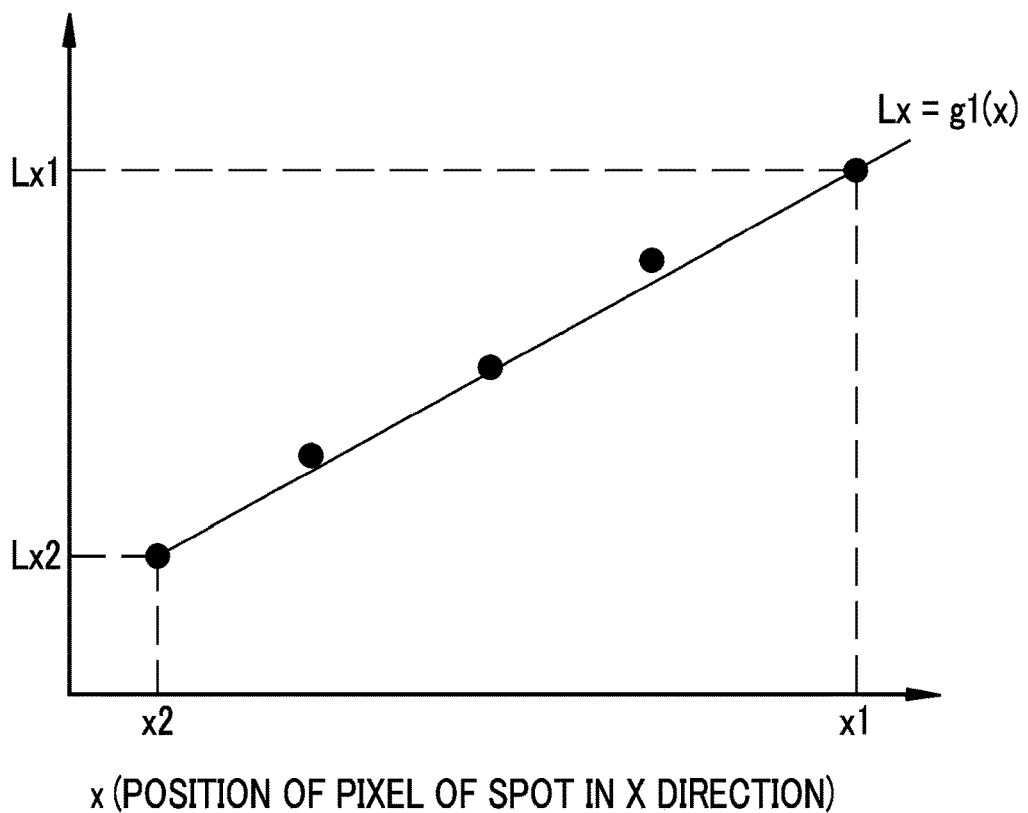
FIG. 18 is a graph showing a relationship between the position of a pixel of a spot in an X direction and the number of pixels of a first measurement marker in the X direction.
Figure 19:
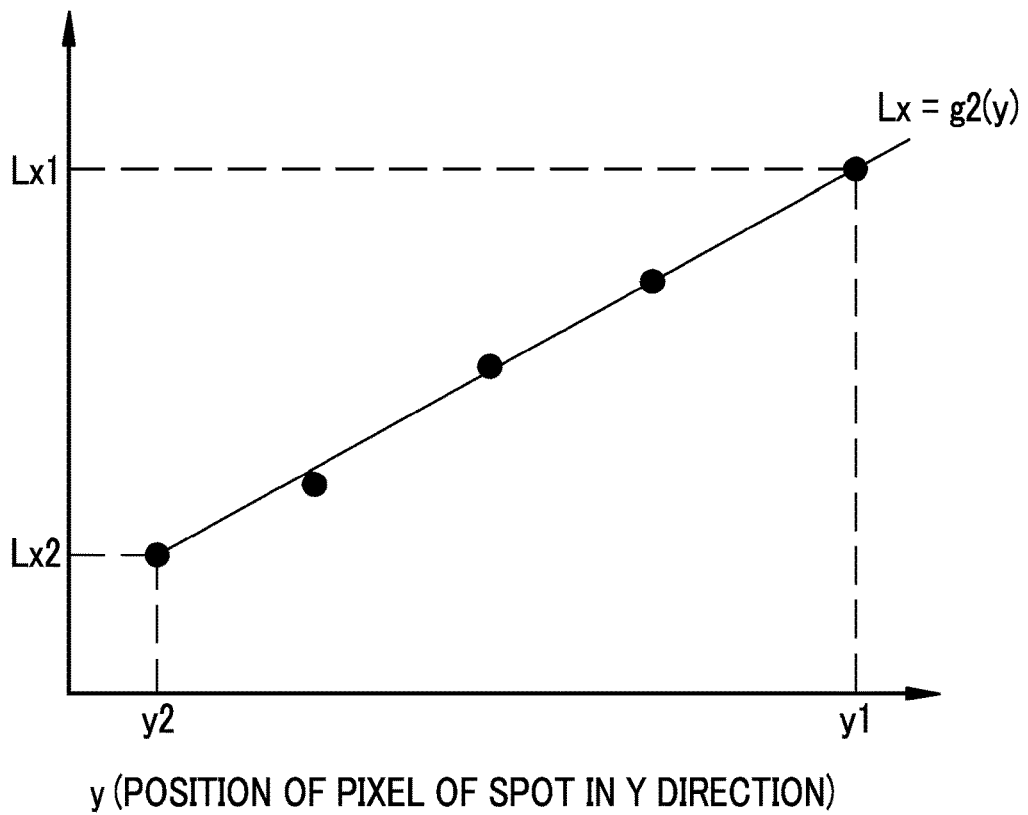
FIG. 19 is a graph showing a relationship between the position of a pixel of a spot in a Y direction and the number of pixels of a first measurement marker in the X direction.

FIG. 18 shows a relationship between the X-coordinate of the position of a spot and Lx (the number of pixels in the X direction), and FIG. 19 shows a relationship between the Y-coordinate of the position of a spot and Lx. Lx is expressed as Lx=g1(x) from the relationship shown in FIG. 18 as the function of a position in the X direction, and Lx is expressed as Lx=g2(y) from the relationship shown in FIG. 19 as the function of a position in the Y direction. g1 and g2 can be obtained from the above-mentioned plotted results by, for example, a least square method.

Since the X-coordinate and the Y-coordinate of a spot have a one-to-one correspondence, basically the same results (the same number of pixels for the same position of a spot) are obtained even though any one of the function g1 or g2 is used. Accordingly, in a case where the size of the first measurement marker is to be calculated, either function may be used and a function having higher sensitivity of a change in the number of pixels to a change in a position may be selected between g1 and g2. Further, in a case where the values of g1 and g2 are significantly different from each other, it may be determined that "the position of a spot could not be recognized".

Figure 20:
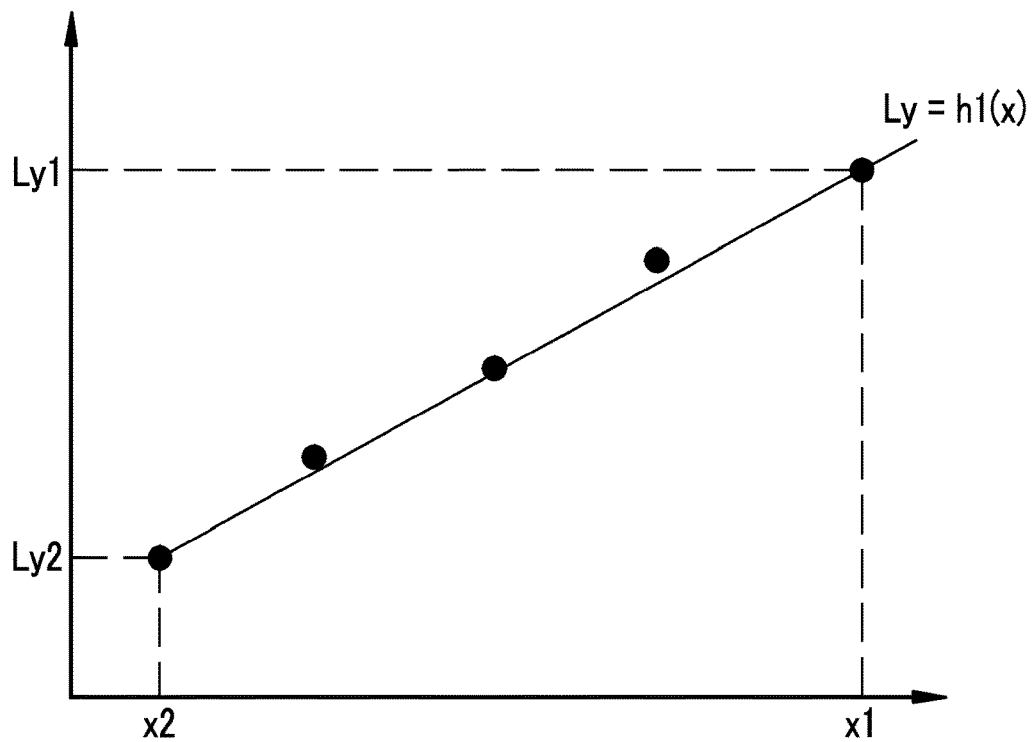
FIG. 20 is a graph showing a relationship between the position of a pixel of a spot in the X direction and the number of pixels of a first measurement marker in the Y direction.
Figure 21:
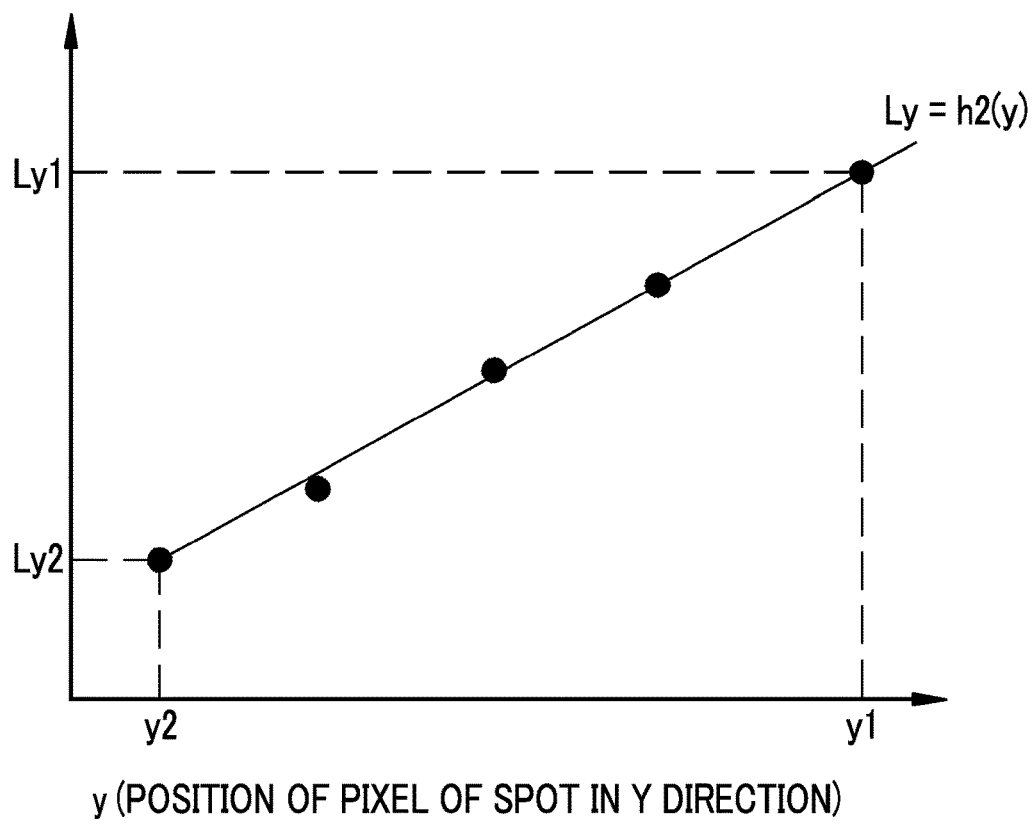
FIG. 21 is a graph showing a relationship between the position of a pixel of a spot in the Y direction and the number of pixels of a first measurement marker in the Y direction.

FIG. 20 shows a relationship between the X-coordinate of the position of a spot and Ly (the number of pixels in the Y direction), and FIG. 21 shows a relationship between the Y-coordinate of the position of a spot and Ly. Ly is expressed as Ly=h1(x) from the relationship shown in FIG. 20 as the coordinate of a position in the X direction, and Ly is expressed as Ly=h2(y) from the relationship shown in FIG. 21 as the coordinate of a position in the Y direction. Any one of the function h1 or h2 may be used as Ly as with Lx.

The functions g1, g2, h1, and h2 obtained as described above are stored in the marker table in a look-up table format. The functions g1 and g2 may be stored in the marker table in a function format.

Figure 22:
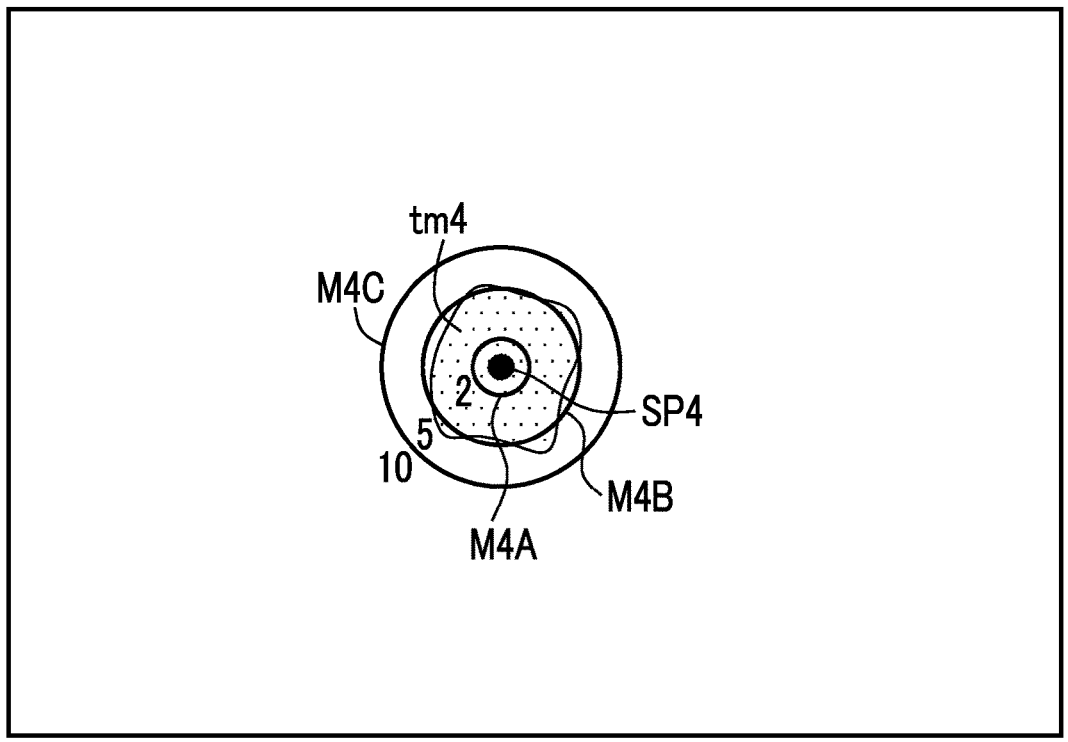
FIG. 22 is an image diagram showing three concentric circular markers having the same color.

As shown in FIG. 22, three concentric circular markers M4A, M4B, and M4C having different sizes (diameters as the sizes are 2 mm, 5 mm, and 10 mm, respectively) may be displayed in the picked-up image as the first measurement marker so that a spot SP4 formed on a tumor tm4 is positioned at the centers of the markers. Since the three concentric circular markers are displayed as a plurality of markers, time and effort required to switch a marker can be saved and measurement can be performed even in a case where a subject has a non-linear shape. In a case where a plurality of concentric circular markers are to be displayed so that a spot is positioned at the centers of the concentric circular markers, a size and a color are not designated for each marker and combinations of a plurality of conditions may be prepared in advance and one can be selected from these combinations.

Figure 23:
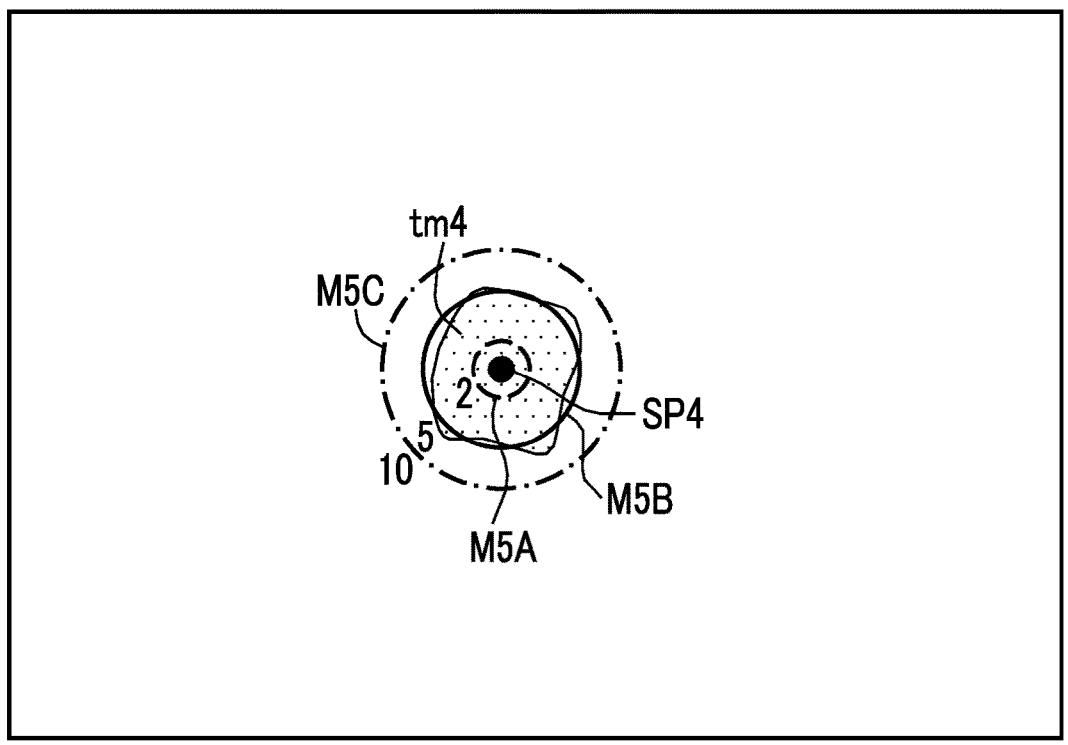
FIG. 23 is an image diagram showing three concentric circular markers having different colors.

In FIG. 22, all the three concentric circular markers are displayed with the same color (black). However, in a case where a plurality of concentric circular markers are to be displayed, a plurality of color concentric circular markers of which colors are different from each other may be used. As shown in FIG. 23, a marker M5A is displayed by a dotted line representing a red color, a marker M5B is displayed by a solid line representing a blue color, and a marker M5C is displayed by a one-dot chain line representing a white color. Since identifiability can be improved in a case where the colors of the markers are different from each other in this way, measurement can be easily performed.

Figure 24:
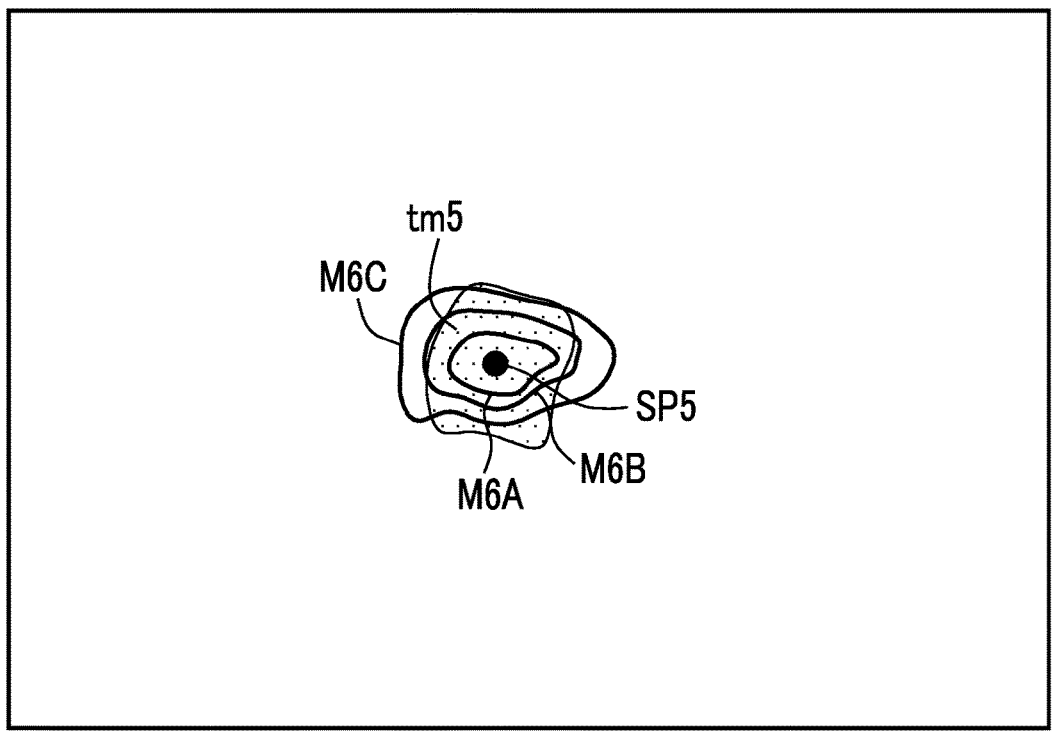
FIG. 24 is an image diagram showing distorted concentric circular markers.

Further, as shown in FIG. 24, a plurality of distorted concentric circular markers, which are distorted from the respective concentric circles, may be used as the first measurement marker other than the plurality of concentric circular markers. In this case, distorted concentric circular markers M6A, M6B, and M6C are displayed in the picked-up image so that a spot SP5 formed on a tumor tm5 is positioned at the centers of the distorted concentric circular markers.

Figure 25:
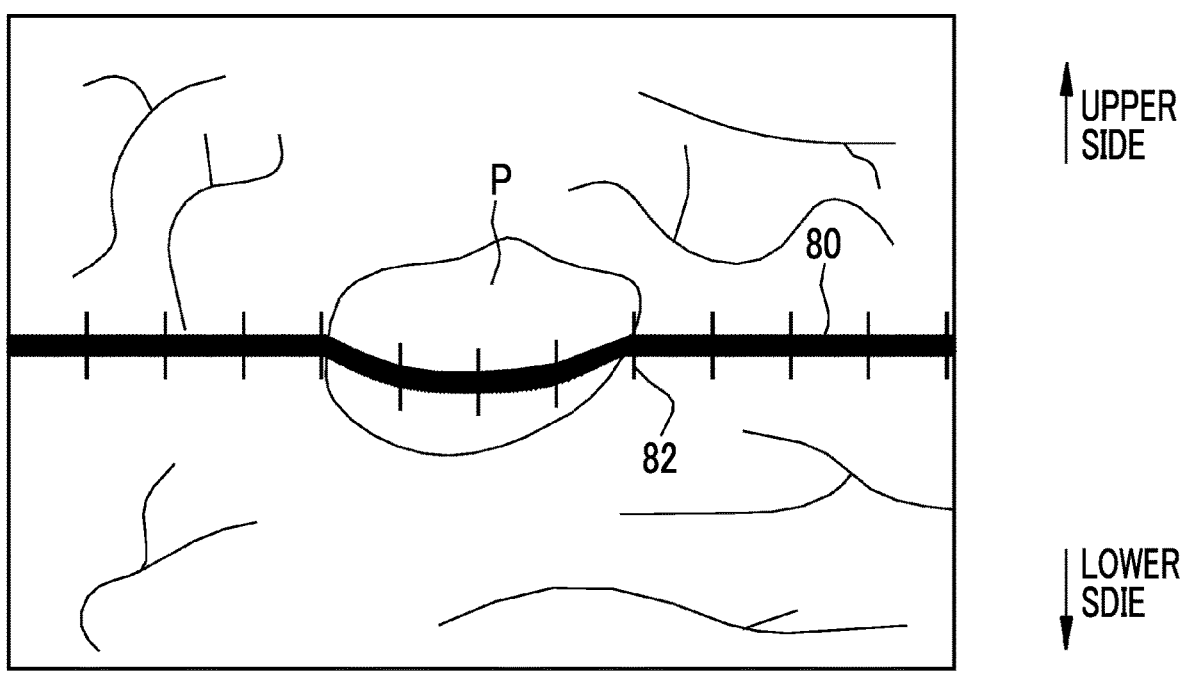
FIG. 25 is an image diagram showing a crossing line and gradations.

Light that forms a spot in a case where a subject is irradiated with the light is used as auxiliary measurement light, but other light may be used. For example, planar auxiliary measurement light that forms a crossing line 80 on a subject as shown in FIG. 25 may be used in a case where the subject is irradiated with light. In this case, a second measurement marker that consists of the crossing line 80 and gradations 82 formed on the crossing line and serving as an index of the size of the subject (for example, a polyp P) is generated as a measurement marker. In a case where planar auxiliary measurement light is used, the irradiation position-detection section 58 detects the position of the crossing line 80 (the irradiation position of auxiliary measurement light). An observation distance is shorter as the crossing line 80 is positioned closer to the lower side, and an observation distance is longer as the crossing line 80 is positioned closer to the upper side. For this reason, an interval between the gradations 82 is larger as the crossing line 80 is positioned closer to the lower side, and an interval between the gradations 82 is smaller as the crossing line 80 is positioned closer to the upper side.

In the embodiment, the hardware structures of processing units, which perform various kinds of processing, such as the signal processing unit 39, the display control unit 40, and the system control unit 41, are various processors to be described later. Various processors include: a central processing unit (CPU) that is a general-purpose processor functioning as various processing units by executing software (program); a programmable logic device (PLD) that is a processor of which the circuit configuration can be changed after manufacture, such as a field programmable gate array (FPGA); a dedicated electrical circuit that is a processor having circuit configuration designed exclusively to perform various kinds of processing; and the like.

One processing unit may be formed of one of these various processors, or may be formed of a combination of two or more same kind or different kinds of processors (for example, a plurality of FPGAs, or a combination of a CPU and an FPGA). Further, a plurality of processing units may be formed of one processor. As an example where a plurality of processing units are formed of one processor, first, there is an aspect where one processor is formed of a combination of one or more CPUs and software as typified by a computer, such as a client or a server, and functions as a plurality of processing units. Second, there is an aspect where a processor fulfilling the functions of the entire system, which includes a plurality of processing units, by one integrated circuit (IC) chip as typified by System On Chip (SoC) or the like is used. In this way, various processing units are formed using one or more of the above-mentioned various processors as hardware structures.

In addition, the hardware structures of these various processors are more specifically electrical circuitry where circuit elements, such as semiconductor elements, are combined. Further, the hardware structure of the storage unit is a storage device, such as a hard disc drive (HDD) or a solid state drive (SSD).

EXPLANATION OF REFERENCES

10: endoscope apparatus
12: endoscope
12a: insertion part
12b: operation part 12c: bendable part
12d: distal end part
12e: angle knob
13a: mode changeover switch
13b: freeze switch
14: light source device
16: processor device
18: monitor
19: user interface
21: objective lens
22: illumination lens
23: auxiliary measurement lens
24: opening
25: air/water supply nozzle
26: illumination light source unit
27: light source control unit
28: light guide
29a: illumination optical system
29b: image pickup optical system
30: auxiliary measurement light-emitting unit
30a: light source
30c: prism
32: image pickup element
33: image pickup control unit
34: CDS/AGC circuit
36: communication I/F
37: static image storage unit
38: communication I/F
39: signal processing unit
40: display control unit
41: system control unit
50: first signal processing section
52: second signal processing section
53: mask processing section
54: binarization processing section
56: noise component-removal section
58: irradiation position-detection section
62: marker table
80: crossing line
101: solid line
102: dotted line
M1, M2, M3: cruciform marker
tm1, tm2, tm3, tm4, tm5: tumor
SP: spot
SP1, SP2, SP3, SP4, SP5: spot
Lx1, Lx2: number of pixels in X direction
Ly1, Ly2: number of pixels in Y direction
M4A, M4B, M4C, M5A, M5B, M5C: concentric circular marker
M6A, M6B, M6C: distorted concentric circular marker
N1: first noise component
N2: second noise component
P: polyp
PRx: red image
PRy: binarized red image
PGx: green image
PGy: binarized green image
PBx: blue image
PBy: binarized blue image
PD1: first difference image
PD2: second difference image
Wx: illumination position-movable range
Wy: specific range

What is claimed is:

1. An endoscope apparatus comprising:
   an illumination light source unit that emits illumination light used to illuminate a subject;
   an auxiliary measurement light source unit that emits auxiliary measurement light;
   an image pickup optical system, wherein an optical axis of the auxiliary measurement light crosses an optical axis of the image pickup optical system; and
   one or more processors configured to:
   acquire a picked-up image that is obtained from image pickup of the subject illuminated with both the illumination light and the auxiliary measurement light and includes at least first and second spectral images having different wavelength components, wherein the first and second spectral images include a spot which is a component of the auxiliary measurement light;
   obtain a first arithmetic image from which a first noise component hindering detection of a position of the spot is removed by first arithmetic processing based on the first and second spectral images;
   detect the position of the spot from the first arithmetic image; and
   display a specific image in which a measurement marker set differently depending on an observation distance indicated by the position of the spot is superimposed on the picked-up image,
   wherein in a case where the one or more processors perform first binarization processing of obtaining a binarized first spectral image by binarizing the first spectral image and second binarization processing of obtaining a binarized second spectral image by binarizing the second spectral image, the one or more processors perform first difference processing of the binarized first spectral image and the binarized second spectral image as the first arithmetic processing, and
   wherein the first spectral image is a red image and the second spectral image is a green image, and the first noise component is a high-brightness component of a red component of the illumination light.

2. The endoscope apparatus according to claim 1,
   wherein the picked-up image includes a third spectral image having a wavelength component different from the wavelength components of the first and second spectral images, and
   the one or more processors obtain a second arithmetic image from which a second noise component different from the first noise component is removed by second arithmetic processing based on the first arithmetic image and the third spectral image.

3. The endoscope apparatus according to claim 2,
   wherein in a case where the one or more processors perform third binarization processing of obtaining a binarized third spectral image by binarizing the third spectral image, the one or more processors perform second difference processing of the first arithmetic image and the binarized third spectral image as the second arithmetic processing.

4. The endoscope apparatus according to claim 2,
   wherein the third spectral image is a blue image.

5. The endoscope apparatus according to claim 1,
   wherein a threshold value condition for the first binarization processing is changed by a histogram of the first spectral image, and
   a threshold value condition for the second binarization processing is changed by a histogram of the second spectral image.

6. The endoscope apparatus according to claim 3,
wherein a threshold value condition for the third binarization processing is changed by a histogram of the third spectral image.
7. The endoscope apparatus according to claim 5,
wherein the histogram is a histogram of an image, which corresponds to a specific range other than an illumination position-movable range of the auxiliary measurement light, in the picked-up image.
8. The endoscope apparatus according to claim 1,
wherein the measurement marker includes a first measurement marker showing an actual size of the subject or a second measurement marker consisting of a crossing line formed on the subject by the auxiliary measurement light and gradations formed on the crossing line and serving as an index of a size of the subject.

* * * * *